United States Patent
Matsuo et al.

(10) Patent No.: US 6,548,284 B1
(45) Date of Patent: Apr. 15, 2003

(54) MEMBRANE-BOUND METALLOPROTEASE AND SOLUBLE SECRETED FORM THEREOF

(75) Inventors: Masafumi Matsuo, 3-31, Kitaochiai 5-chome, Suma-ku, Kobe, Hyogo 654-0151 (JP); Koji Ikeda, Kobe (JP); Noriaki Emoto, Ashiya (JP); Sunu Budhi Raharjo, Kobe (JP); Yudha Nurhantari, Kobe (JP); Kayoko Saiki, Takarazuka (JP); Mitsuhiro Yokoyama, Kobe (JP)

(73) Assignees: JCR Pharmaceuticals Co., Ltd., Hyogo (JP); Masafumi Matsuo, Hyogo (JP)

( * ) Notice: Subject to any disclaimer, the term of this patent is extended or adjusted under 35 U.S.C. 154(b) by 28 days.

(21) Appl. No.: 09/704,611

(22) Filed: Nov. 3, 2000

(30) Foreign Application Priority Data

Apr. 4, 2000 (JP) ......................................... 2000-101776

(51) Int. Cl.[7] ........................ C12N 9/64; C12N 15/57; C12N 15/63; C12N 15/79

(52) U.S. Cl. ................... 435/226; 435/69.1; 435/252.3; 435/320.1; 536/23.2

(58) Field of Search ............................... 435/226, 69.1, 435/252.3, 320.1; 424/94.67; 536/23.2

(56) References Cited

FOREIGN PATENT DOCUMENTS

WO  WO 99/53077  * 10/1999

OTHER PUBLICATIONS

Ikeda et al., 1999, "Molecular identification and characterization of novel membrane–bound metalloprotese, the soluble secreted form of which hydrolyzes a variety of vasoactive peptides", The Journal of Biological Chemistry, vol. 274, pp. 32469–32477.*

Ghaddar et al., 2000, "Molecular cloning and biochemical characterization of a new mouse testis soluble–zinc–metallopeptidase of the neprilysin family", Biochemical Journal, vol. 347, pp. 419–429.*

Tanja et al., 2000, "Neprilysin II: A putative novel metalloprotease and its isoforms in SNC and testis", Biochemical and Biophysical Research Communications, vol. 271, pp. 565–570.*

Marra et al., 1998, EST Database Accession No. Al325325, 705 bp. Soares mouse cDNA clone IMAGE:31340, 5' similar to human neprilysin, nucleotide sequence positions 9–698.*

Hooper, N.M., FEBS, vol. 354, 41–6(1994).
Yanagisawa, M., Circulation, vol. 89, 1320–1322 (1994).
Turner, A.J. and Murphy, J.J., Biochem. Pharmacol., vol. 51, 91–102 (1996).
Turner, A.J. and Tanazawa, K., FASEB J., vol. 11, 355–364 (1997).
Roques, B.P., et al., Pharmacol. Rev., vol. 45, No. 1, 87–146 (1993).
Lu, B., et al., J. Exp. Med., vol. 181, 2271–2275 (1995).
Lu, B., et al., Nature Med., vol. 3, No. 8, 904–907 (1997).

(List continued on next page.)

Primary Examiner—Ponnathapu Achutamurthy
Assistant Examiner—William W. Moore
(74) Attorney, Agent, or Firm—Greenblum & Bernstein, P.L.C.

(57) ABSTRACT

Disclosed are metalloprotease proteins or their salts usable for treatment or prophylaxis of conformational diseases and for providing a screening kit for selection of carcinostatics and anti-metastatic agents. The metalloprotease proteins have an amino acid sequence set forth under SEQ ID NO:1 or NO:2 in the Sequence Listing. The proteins have a neutral optimal pH, hydrolyze endothelin 1, atrial natriuretic peptide and angiotensin I and are inhibited by 1,10-phenanthroline, phosphoramidon and thiorphan.

9 Claims, 6 Drawing Sheets

OTHER PUBLICATIONS

Yanagisawa, M., et al., Nature, vol. 332, 411–415 (1988).

Xu, D., et al., Cell, vol. 78, 473–485 (1994).

Emoto, N. and Yanagisawa, M., J. Biol. Chem., vol. 270, No. 25, 15262–15268 (1995).

Yanagisawa, H., et al., Development, vol. 125, 825–836 (1998).

Current Protocols in Molecular Biology, vol. 1, Chapter 8, Edited by Ausubel, F.M., John Wiley & Sons, Inc., 8.0.1–8.5.10.

Gacesa, P. and Ramji, D.P., Expression Vectors, Vectors Essential Data, BIOS Scientific Publishers Ltd., John Wiley & Sons, 9–12.

Current Protocols in Molecular Biology, vol. 2, Chapter 11, Edited by Ausubel, F.M., John Wiley & Sons, Inc., 11.0.1–11.16.13.

Emoto, N., et al., J. Biol. Chem., vol. 274, No. 3, 1509–1518 (1999).

* cited by examiner

SEQUENCE LISTING

<160> NUMBER OF SEQ ID NOS: 9

<210> SEQ ID NO 1
<211> LENGTH: 765
<212> TYPE: PRT
<213> ORGANISM: Mus musculus

<400> SEQUENCE: 1

```
Met Val Glu Arg Ala Gly Trp Cys Arg Lys Lys Ser Pro Gly Phe Val
 1               5                  10                  15

Glu Tyr Gly Leu Met Val Leu Leu Leu Leu Leu Gly Ala Ile Val
             20                  25                  30

Thr Leu Gly Val Phe Tyr Ser Ile Gly Lys Gln Leu Pro Leu Leu Thr
             35                  40                  45

Ser Leu Leu His Phe Ser Trp Asp Glu Arg Thr Val Val Lys Arg Ala
     50                  55                  60

Leu Arg Asp Ser Ser Leu Lys Ser Asp Ile Cys Thr Thr Pro Ser Cys
65                   70                  75                  80

Val Ile Ala Ala Ala Arg Ile Leu Glu Asn Met Asp Gln Ser Arg Asn
                 85                  90                  95

Pro Cys Glu Asn Phe Tyr Gln Tyr Ala Cys Gly Gly Trp Leu Arg His
            100                 105                 110
```

-continued

```
His Val Ile Pro Glu Thr Asn Ser Arg Tyr Ser Val Phe Asp Ile Leu
            115                 120                 125
Arg Asp Glu Leu Glu Val Ile Leu Lys Gly Val Leu Glu Asp Ser Thr
130                 135                 140
Ser Gln His Arg Pro Ala Val Glu Lys Ala Lys Thr Leu Tyr Arg Ser
145                 150                 155                 160
Cys Met Asn Gln Ser Val Ile Glu Lys Arg Asp Ser Glu Pro Leu Leu
                165                 170                 175
Ser Val Leu Lys Met Val Gly Gly Trp Pro Val Ala Leu Asp Lys Trp
            180                 185                 190
Asn Glu Thr Met Gly Leu Lys Trp Glu Leu Glu Arg Gln Leu Ala Val
            195                 200                 205
Leu Asn Ser Gln Phe Asn Arg Arg Val Leu Ile Asp Leu Phe Ile Trp
210                 215                 220
Asn Asp Asp Gln Asn Ser Ser Arg His Val Ile Tyr Ile Asp Gln Pro
225                 230                 235                 240
Thr Leu Gly Met Pro Ser Arg Glu Tyr Tyr Phe Gln Glu Asp Asn Asn
                245                 250                 255
His Lys Val Arg Lys Ala Tyr Pro Glu Phe Met Thr Ser Val Ala Thr
            260                 265                 270
Met Leu Arg Lys Asp Gln Asn Leu Ser Lys Glu Ser Ala Met Val Arg
            275                 280                 285
Glu Glu Met Ala Glu Val Leu Glu Leu Glu Thr His Leu Ala Asn Ala
            290                 295                 300
Thr Val Pro Gln Glu Lys Arg His Asp Val Thr Ala Leu Tyr His Arg
305                 310                 315                 320
Met Asp Leu Met Glu Leu Gln Glu Arg Phe Gly Leu Lys Gly Phe Asn
                325                 330                 335
Trp Thr Leu Phe Ile Gln Asn Val Leu Ser Ser Val Glu Val Glu Leu
            340                 345                 350
Phe Pro Asp Glu Glu Val Val Tyr Gly Ile Pro Tyr Leu Glu Asn
            355                 360                 365
Leu Glu Asp Ile Ile Asp Ser Tyr Ser Ala Arg Thr Met Gln Asn Tyr
370                 375                 380
Leu Val Trp Arg Leu Val Leu Asp Arg Ile Gly Ser Leu Ser Gln Arg
385                 390                 395                 400
Phe Lys Glu Ala Arg Val Asp Tyr Arg Lys Ala Leu Tyr Gly Thr Thr
                405                 410                 415
Val Glu Glu Val Arg Trp Arg Glu Cys Val Ser Tyr Val Asn Ser Asn
            420                 425                 430
Met Glu Ser Ala Val Gly Ser Leu Tyr Ile Lys Arg Ala Phe Ser Lys
            435                 440                 445
Asp Ser Lys Ser Thr Val Arg Glu Leu Ile Glu Lys Ile Arg Ser Val
450                 455                 460
Phe Val Asp Asn Leu Asp Glu Leu Asn Trp Met Asp Glu Glu Ser Lys
465                 470                 475                 480
Lys Lys Ala Gln Glu Lys Ala Met Asn Ile Arg Glu Gln Ile Gly Tyr
                485                 490                 495
Pro Asp Tyr Ile Leu Glu Asp Asn Lys His Leu Asp Glu Glu Tyr
            500                 505                 510
Ser Ser Leu Thr Phe Tyr Glu Asp Leu Tyr Phe Glu Asn Gly Leu Gln
            515                 520                 525
```

-continued

```
Asn Leu Lys Asn Asn Ala Gln Arg Ser Leu Lys Lys Leu Arg Glu Lys
        530                 535                 540

Val Asp Gln Asn Leu Trp Ile Ile Gly Ala Ala Val Val Asn Ala Phe
545                 550                 555                 560

Tyr Ser Pro Asn Arg Asn Gln Ile Val Phe Pro Ala Gly Ile Leu Gln
                565                 570                 575

Pro Pro Phe Phe Ser Lys Asp Gln Pro Gln Ser Leu Asn Phe Gly Gly
            580                 585                 590

Ile Gly Met Val Ile Gly His Glu Ile Thr His Gly Phe Asp Asp Asn
        595                 600                 605

Gly Arg Asn Phe Asp Lys Asn Gly Asn Met Leu Asp Trp Trp Ser Asn
    610                 615                 620

Phe Ser Ala Arg His Phe Gln Gln Gln Ser Gln Cys Met Ile Tyr Gln
625                 630                 635                 640

Tyr Gly Asn Phe Ser Trp Glu Leu Ala Asp Asn Gln Asn Val Asn Gly
                645                 650                 655

Phe Ser Ser Leu Gly Glu Asn Ile Ala Asp Asn Gly Val Arg Gln
            660                 665                 670

Ala Tyr Lys Ala Tyr Leu Arg Trp Leu Ala Asp Gly Gly Lys Asp Gln
        675                 680                 685

Arg Leu Pro Gly Leu Asn Leu Thr Tyr Ala Gln Leu Phe Phe Ile Asn
    690                 695                 700

Tyr Ala Gln Val Trp Cys Gly Ser Tyr Arg Pro Glu Phe Ala Val Gln
705                 710                 715                 720

Ser Ile Lys Thr Asp Val His Ser Pro Leu Lys Tyr Arg Val Leu Gly
                725                 730                 735

Ser Leu Gln Asn Leu Pro Gly Phe Ser Glu Ala Phe His Cys Pro Arg
            740                 745                 750

Gly Ser Pro Met His Pro Met Lys Arg Cys Arg Ile Trp
        755                 760                 765

<210> SEQ ID NO 2
<211> LENGTH: 742
<212> TYPE: PRT
<213> ORGANISM: Mus musculus

<400> SEQUENCE: 2

Met Val Glu Arg Ala Gly Trp Cys Arg Lys Lys Ser Pro Gly Phe Val
1               5                   10                  15

Glu Tyr Gly Leu Met Val Leu Leu Leu Leu Leu Gly Ala Ile Val
                20                  25                  30

Thr Leu Gly Val Phe Tyr Ser Ile Ala Leu Arg Asp Ser Ser Leu Lys
            35                  40                  45

Ser Asp Ile Cys Thr Thr Pro Ser Cys Val Ile Ala Ala Ala Arg Ile
        50                  55                  60

Leu Glu Asn Met Asp Gln Ser Arg Asn Pro Cys Glu Asn Phe Tyr Gln
65                  70                  75                  80

Tyr Ala Cys Gly Gly Trp Leu Arg His His Val Ile Pro Glu Thr Asn
                85                  90                  95

Ser Arg Tyr Ser Val Phe Asp Ile Leu Arg Asp Glu Leu Glu Val Ile
                100                 105                 110

Leu Lys Gly Val Leu Glu Asp Ser Thr Ser Gln His Arg Pro Ala Val
            115                 120                 125

Glu Lys Ala Lys Thr Leu Tyr Arg Ser Cys Met Asn Gln Ser Val Ile
        130                 135                 140
```

-continued

```
Glu Lys Arg Asp Ser Glu Pro Leu Leu Ser Val Leu Lys Met Val Gly
145                 150                 155                 160

Gly Trp Pro Val Ala Leu Asp Lys Trp Asn Glu Thr Met Gly Leu Lys
                165                 170                 175

Trp Glu Leu Glu Arg Gln Leu Ala Val Leu Asn Ser Gln Phe Asn Arg
            180                 185                 190

Arg Val Leu Ile Asp Leu Phe Ile Trp Asn Asp Asp Gln Asn Ser Ser
        195                 200                 205

Arg His Val Ile Tyr Ile Asp Gln Pro Thr Leu Gly Met Pro Ser Arg
    210                 215                 220

Glu Tyr Tyr Phe Gln Glu Asp Asn Asn His Lys Val Arg Lys Ala Tyr
225                 230                 235                 240

Pro Glu Phe Met Thr Ser Val Ala Thr Met Leu Arg Lys Asp Gln Asn
                245                 250                 255

Leu Ser Lys Glu Ser Ala Met Val Arg Glu Met Ala Glu Val Leu
            260                 265                 270

Glu Leu Glu Thr His Leu Ala Asn Ala Thr Val Pro Gln Glu Lys Arg
        275                 280                 285

His Asp Val Thr Ala Leu Tyr His Arg Met Asp Leu Met Glu Leu Gln
    290                 295                 300

Glu Arg Phe Gly Leu Lys Gly Phe Asn Trp Thr Leu Phe Ile Gln Asn
305                 310                 315                 320

Val Leu Ser Ser Val Glu Val Glu Leu Phe Pro Asp Glu Glu Val Val
                325                 330                 335

Val Tyr Gly Ile Pro Tyr Leu Gly Asn Leu Glu Asp Ile Ile Asp Ser
            340                 345                 350

Tyr Ser Ala Arg Thr Met Gln Asn Tyr Leu Val Trp Arg Leu Val Leu
        355                 360                 365

Asp Arg Ile Gly Ser Leu Ser Gln Arg Phe Lys Glu Ala Arg Val Asp
    370                 375                 380

Tyr Arg Lys Ala Leu Tyr Gly Thr Thr Val Glu Glu Val Arg Trp Arg
385                 390                 395                 400

Glu Cys Val Ser Tyr Val Asn Ser Asn Met Glu Ser Ala Val Gly Ser
                405                 410                 415

Leu Tyr Ile Lys Arg Ala Phe Ser Lys Asp Ser Lys Ser Thr Val Arg
            420                 425                 430

Glu Leu Ile Glu Lys Ile Arg Ser Val Phe Val Asp Asn Leu Asp Glu
        435                 440                 445

Leu Asn Trp Met Asp Glu Glu Ser Lys Lys Ala Gln Glu Lys Ala
450                 455                 460

Met Asn Ile Arg Glu Gln Ile Gly Tyr Pro Asp Tyr Ile Leu Glu Asp
465                 470                 475                 480

Asn Asn Lys His Leu Asp Glu Glu Tyr Ser Ser Leu Thr Phe Tyr Glu
                485                 490                 495

Asp Leu Tyr Phe Glu Asn Gly Leu Gln Asn Leu Lys Asn Asn Ala Gln
            500                 505                 510

Arg Ser Leu Lys Lys Leu Arg Glu Lys Val Asp Gln Asn Leu Trp Ile
        515                 520                 525

Ile Gly Ala Ala Val Val Asn Ala Phe Tyr Ser Pro Asn Arg Asn Gln
    530                 535                 540

Ile Val Phe Pro Ala Gly Ile Leu Gln Pro Pro Phe Phe Ser Lys Asp
545                 550                 555                 560
```

-continued

```
Gln Pro Gln Ser Leu Asn Phe Gly Gly Ile Gly Met Val Ile Gly His
            565                 570                 575

Glu Ile Thr His Gly Phe Asp Asp Asn Gly Arg Asn Phe Asp Lys Asn
            580                 585                 590

Gly Asn Met Leu Asp Trp Trp Ser Asn Phe Ser Ala Arg His Phe Gln
            595                 600                 605

Gln Gln Ser Gln Cys Met Ile Tyr Gln Tyr Gly Asn Phe Ser Trp Glu
    610                 615                 620

Leu Ala Asp Asn Gln Asn Val Asn Gly Phe Ser Ser Leu Gly Glu Asn
625                 630                 635                 640

Ile Ala Asp Asn Gly Gly Val Arg Gln Ala Tyr Lys Ala Tyr Leu Arg
                645                 650                 655

Trp Leu Ala Asp Gly Gly Lys Asp Gln Arg Leu Pro Gly Leu Asn Leu
                660                 665                 670

Thr Tyr Ala Gln Leu Phe Phe Ile Asn Tyr Ala Gln Val Trp Cys Gly
                675                 680                 685

Ser Tyr Arg Pro Glu Phe Ala Val Gln Ser Ile Lys Thr Asp Val His
                690                 695                 700

Ser Pro Leu Lys Tyr Arg Val Leu Gly Ser Leu Gln Asn Leu Pro Gly
705                 710                 715                 720

Phe Ser Glu Ala Phe His Cys Pro Arg Gly Ser Pro Met His Pro Met
                725                 730                 735

Lys Arg Cys Arg Ile Trp
            740
```

<210> SEQ ID NO 3
<211> LENGTH: 2892
<212> TYPE: DNA
<213> ORGANISM: Mus musculus

<400> SEQUENCE: 3

```
ccggagccca ccttggccag ctcaccccaa ctctgagaca tcccaaccta gcctttaagg      60
acttgcctag aagtgactga gagcaccagg gtcccctggg cacttggggc acagcttaca     120
gcattgagag cagagaccag gacagtgcac cagcttcagt gtgtcctagg catccgatcc     180
gggctccagc tgcctctctc ctagccctgg cctgggggggc ttagcggtgt gccttccacc    240
cagaaccggc tgatagggaa agtctgagag cccagtgggg atg gtg gag aga gca      295
                                             Met Val Glu Arg Ala
                                               1               5 ggc tgg tgt cgg aag aag tcc cca ggc ttc gtg gag tat ggg ctg atg      343
Gly Trp Cys Arg Lys Lys Ser Pro Gly Phe Val Glu Tyr Gly Leu Met
             10                  15                  20 gtg ctg ctg ctg ctg ttg ctg gga gcc ata gtg act ctg ggt gtc ttc      391
Val Leu Leu Leu Leu Leu Leu Gly Ala Ile Val Thr Leu Gly Val Phe
         25                  30                  35 tac agc ata ggg aag cag ctg ccc ctc tta act agc ctg cta cac ttc      439
Tyr Ser Ile Gly Lys Gln Leu Pro Leu Leu Thr Ser Leu Leu His Phe
     40                  45                  50 tcc tgg gat gag agg acg gtt gta aaa cga gcc ctc agg gat tca tca      487
Ser Trp Asp Glu Arg Thr Val Val Lys Arg Ala Leu Arg Asp Ser Ser
 55                  60                  65 ctg aaa agt gac atc tgc acc acc cca agc tgt gtg ata gca gct gcc      535
Leu Lys Ser Asp Ile Cys Thr Thr Pro Ser Cys Val Ile Ala Ala Ala
 70                  75                  80                  85 aga atc ctc gaa aac atg gac caa tcg agg aac ccc tgt gaa aac ttc      583
Arg Ile Leu Glu Asn Met Asp Gln Ser Arg Asn Pro Cys Glu Asn Phe
                 90                  95                 100
```

```
tac cag tac gcc tgc gga ggc tgg ctg agg cac cac gtg atc cca gag      631
Tyr Gln Tyr Ala Cys Gly Gly Trp Leu Arg His His Val Ile Pro Glu
            105                 110                 115 acc aac tcc cga tac agc gtc ttt gac atc ctg cgg gac gag ctg gag      679
Thr Asn Ser Arg Tyr Ser Val Phe Asp Ile Leu Arg Asp Glu Leu Glu
        120                 125                 130 gtt atc ctc aaa ggg gtg ctg gag gat tcc act tcc cag cat cgc ccg      727
Val Ile Leu Lys Gly Val Leu Glu Asp Ser Thr Ser Gln His Arg Pro
    135                 140                 145 gcc gtg gag aag gcc aag aca cta tat cgc tcc tgc atg aac caa agt      775
Ala Val Glu Lys Ala Lys Thr Leu Tyr Arg Ser Cys Met Asn Gln Ser
150                 155                 160                 165 gtg atc gag aag aga gac tct gag ccc ctg ctg agc gtc tta aaa atg      823
Val Ile Glu Lys Arg Asp Ser Glu Pro Leu Leu Ser Val Leu Lys Met
            170                 175                 180 gta gga ggt tgg cct gtg gca ttg gat aag tgg aac gag acc atg ggc      871
Val Gly Gly Trp Pro Val Ala Leu Asp Lys Trp Asn Glu Thr Met Gly
        185                 190                 195 ctc aag tgg gaa ctg gag cga cag ttg gct gtg ttg aac tcg cag ttc      919
Leu Lys Trp Glu Leu Glu Arg Gln Leu Ala Val Leu Asn Ser Gln Phe
    200                 205                 210 aac agg cgg gtc ctc atc gac ctc ttc atc tgg aat gac gac cag aac      967
Asn Arg Arg Val Leu Ile Asp Leu Phe Ile Trp Asn Asp Asp Gln Asn
215                 220                 225 tcc agc cgg cat gtc atc tac ata gac cag ccc acc ttg ggc atg cca     1015
Ser Ser Arg His Val Ile Tyr Ile Asp Gln Pro Thr Leu Gly Met Pro
230                 235                 240                 245 tcc cgg gag tac tat ttc cag gag gac aac aac cac aag gta cgg aaa     1063
Ser Arg Glu Tyr Tyr Phe Gln Glu Asp Asn Asn His Lys Val Arg Lys
            250                 255                 260 gcc tac ccg gag ttc atg acg tca gtg gcc act atg ctt agg aaa gac     1111
Ala Tyr Pro Glu Phe Met Thr Ser Val Ala Thr Met Leu Arg Lys Asp
        265                 270                 275 cag aac ctg tcc aag gag agc gcc atg gtg cgg gag gag atg gcg gag     1159
Gln Asn Leu Ser Lys Glu Ser Ala Met Val Arg Glu Glu Met Ala Glu
    280                 285                 290 gtg ctg gaa ctg gag acg cat ctg gcc aac gcc aca gtc ccc cag gag     1207
Val Leu Glu Leu Glu Thr His Leu Ala Asn Ala Thr Val Pro Gln Glu
295                 300                 305 aaa agg cat gat gtc act gcc ctg tac cac cga atg gac ctg atg gag     1255
Lys Arg His Asp Val Thr Ala Leu Tyr His Arg Met Asp Leu Met Glu
310                 315                 320                 325 cta cag gaa agg ttt ggt ctg aag ggg ttt aac tgg act ctc ttc ata     1303
Leu Gln Glu Arg Phe Gly Leu Lys Gly Phe Asn Trp Thr Leu Phe Ile
            330                 335                 340 caa aac gtg ttg tct tct gtg gaa gtc gag ctg ttc cca gat gag gag     1351
Gln Asn Val Leu Ser Ser Val Glu Val Glu Leu Phe Pro Asp Glu Glu
        345                 350                 355 gtg gtg gtc tac ggc atc ccc tac ctg gag aat ctg gag gat atc att     1399
Val Val Val Tyr Gly Ile Pro Tyr Leu Glu Asn Leu Glu Asp Ile Ile
    360                 365                 370 gat agc tac tca gca cgg acc atg cag aac tac ctg gta tgg cgc ctg     1447
Asp Ser Tyr Ser Ala Arg Thr Met Gln Asn Tyr Leu Val Trp Arg Leu
375                 380                 385 gtg cta gat cga att ggc agc ctg agc cag aga ttc aaa gag gcg cgt     1495
Val Leu Asp Arg Ile Gly Ser Leu Ser Gln Arg Phe Lys Glu Ala Arg
390                 395                 400                 405 gtg gac tac cgc aag gcg ctg tac ggc acg acc gtg gag gag gta cgc     1543
Val Asp Tyr Arg Lys Ala Leu Tyr Gly Thr Thr Val Glu Glu Val Arg
```

-continued

|  |  | 410 |  |  |  | 415 |  |  |  | 420 |  |  |  |  |
|---|---|---|---|---|---|---|---|---|---|---|---|---|---|---|
| tgg | cga | gag | tgt | gtc | agc | tat | gtc | aac | agt | aac | atg | gag | agc | gcc | gtg | 1591 |
| Trp | Arg | Glu | Cys | Val | Ser | Tyr | Val | Asn | Ser | Asn | Met | Glu | Ser | Ala | Val |
|  |  | 425 |  |  |  | 430 |  |  |  | 435 |  |  |

| ggc | tcc | ctc | tac | atc | aag | cgg | gcc | ttc | tcc | aag | gac | agc | aag | agc | acg | 1639 |
| Gly | Ser | Leu | Tyr | Ile | Lys | Arg | Ala | Phe | Ser | Lys | Asp | Ser | Lys | Ser | Thr |
|  | 440 |  |  |  | 445 |  |  |  | 450 |

| gtc | aga | gag | ctg | att | gag | aag | ata | agg | tcc | gtg | ttt | gtg | gat | aac | ctg | 1687 |
| Val | Arg | Glu | Leu | Ile | Glu | Lys | Ile | Arg | Ser | Val | Phe | Val | Asp | Asn | Leu |
|  | 455 |  |  |  | 460 |  |  |  | 465 |

| gat | gag | ctg | aac | tgg | atg | gac | gag | gaa | tcc | aag | aag | aag | gcc | cag | gaa | 1735 |
| Asp | Glu | Leu | Asn | Trp | Met | Asp | Glu | Glu | Ser | Lys | Lys | Lys | Ala | Gln | Glu |
| 470 |  |  |  | 475 |  |  |  | 480 |  |  |  | 485 |

| aag | gcc | atg | aat | ata | cgg | gaa | cag | att | ggc | tac | cct | gac | tac | att | ttg | 1783 |
| Lys | Ala | Met | Asn | Ile | Arg | Glu | Gln | Ile | Gly | Tyr | Pro | Asp | Tyr | Ile | Leu |
|  |  | 490 |  |  |  | 495 |  |  |  | 500 |

| gaa | gat | aac | aat | aaa | cac | ctg | gat | gag | gaa | tac | tcc | agt | ttg | act | ttc | 1831 |
| Glu | Asp | Asn | Asn | Lys | His | Leu | Asp | Glu | Glu | Tyr | Ser | Ser | Leu | Thr | Phe |
|  |  | 505 |  |  |  | 510 |  |  |  | 515 |

| tat | gag | gac | ctg | tat | ttt | gag | aac | gga | ctt | cag | aac | ctc | aag | aac | aat | 1879 |
| Tyr | Glu | Asp | Leu | Tyr | Phe | Glu | Asn | Gly | Leu | Gln | Asn | Leu | Lys | Asn | Asn |
|  | 520 |  |  |  | 525 |  |  |  | 530 |

| gcc | cag | agg | agc | ctc | aag | aag | ctt | cgg | gaa | aag | gtg | gac | cag | aat | ctc | 1927 |
| Ala | Gln | Arg | Ser | Leu | Lys | Lys | Leu | Arg | Glu | Lys | Val | Asp | Gln | Asn | Leu |
| 535 |  |  |  | 540 |  |  |  | 545 |

| tgg | atc | atc | ggg | gct | gca | gtg | gtc | aat | gca | ttc | tac | tcc | cca | aac | aga | 1975 |
| Trp | Ile | Ile | Gly | Ala | Ala | Val | Val | Asn | Ala | Phe | Tyr | Ser | Pro | Asn | Arg |
| 550 |  |  |  | 555 |  |  |  | 560 |  |  |  | 565 |

| aac | cag | atc | gtc | ttt | cca | gca | ggg | att | ctc | cag | ccg | ccc | ttc | ttc | agc | 2023 |
| Asn | Gln | Ile | Val | Phe | Pro | Ala | Gly | Ile | Leu | Gln | Pro | Pro | Phe | Phe | Ser |
|  |  | 570 |  |  |  | 575 |  |  |  | 580 |

| aag | gac | caa | cca | cag | tcc | ttg | aat | ttt | ggg | ggc | atc | ggg | atg | gtg | att | 2071 |
| Lys | Asp | Gln | Pro | Gln | Ser | Leu | Asn | Phe | Gly | Gly | Ile | Gly | Met | Val | Ile |
|  |  | 585 |  |  |  | 590 |  |  |  | 595 |

| ggg | cac | gag | atc | aca | cac | ggc | ttt | gat | gat | aat | ggt | cgt | aac | ttt | gac | 2119 |
| Gly | His | Glu | Ile | Thr | His | Gly | Phe | Asp | Asp | Asn | Gly | Arg | Asn | Phe | Asp |
|  | 600 |  |  |  | 605 |  |  |  | 610 |

| aag | aac | ggc | aac | atg | ctg | gac | tgg | tgg | agt | aac | ttc | tcg | gcc | cgg | cac | 2167 |
| Lys | Asn | Gly | Asn | Met | Leu | Asp | Trp | Trp | Ser | Asn | Phe | Ser | Ala | Arg | His |
| 615 |  |  |  | 620 |  |  |  | 625 |

| ttc | caa | cag | cag | tcg | caa | tgc | atg | atc | tat | cag | tac | ggc | aac | ttc | tct | 2215 |
| Phe | Gln | Gln | Gln | Ser | Gln | Cys | Met | Ile | Tyr | Gln | Tyr | Gly | Asn | Phe | Ser |
| 630 |  |  |  | 635 |  |  |  | 640 |  |  |  | 645 |

| tgg | gaa | cta | gca | gac | aac | cag | aat | gtg | aac | gga | ttc | agt | tcc | ctc | ggg | 2263 |
| Trp | Glu | Leu | Ala | Asp | Asn | Gln | Asn | Val | Asn | Gly | Phe | Ser | Ser | Leu | Gly |
|  |  | 650 |  |  |  | 655 |  |  |  | 660 |

| gag | aac | att | gcc | gac | aac | gga | ggt | gtg | cga | cag | gca | tac | aag | gct | tac | 2311 |
| Glu | Asn | Ile | Ala | Asp | Asn | Gly | Gly | Val | Arg | Gln | Ala | Tyr | Lys | Ala | Tyr |
|  |  | 665 |  |  |  | 670 |  |  |  | 675 |

| cta | cgg | tgg | ctg | gct | gat | ggc | ggc | aaa | gat | cag | cga | ctg | ccg | gga | ctg | 2359 |
| Leu | Arg | Trp | Leu | Ala | Asp | Gly | Gly | Lys | Asp | Gln | Arg | Leu | Pro | Gly | Leu |
|  | 680 |  |  |  | 685 |  |  |  | 690 |

| aac | ctg | acc | tat | gcc | cag | ctt | ttc | ttc | atc | aac | tat | gcc | cag | gtg | tgg | 2407 |
| Asn | Leu | Thr | Tyr | Ala | Gln | Leu | Phe | Phe | Ile | Asn | Tyr | Ala | Gln | Val | Trp |
|  | 695 |  |  |  | 700 |  |  |  | 705 |

| tgt | ggg | tcc | tat | agg | ccg | gag | ttc | gcc | gtc | cag | tcc | atc | aag | acg | gac | 2455 |
| Cys | Gly | Ser | Tyr | Arg | Pro | Glu | Phe | Ala | Val | Gln | Ser | Ile | Lys | Thr | Asp |
| 710 |  |  |  | 715 |  |  |  | 720 |  |  |  | 725 |

| gtc | cac | agt | cct | ctt | aag | tac | agg | gtg | ctg | ggc | tca | cta | cag | aac | ctg | 2503 |

```
Val His Ser Pro Leu Lys Tyr Arg Val Leu Gly Ser Leu Gln Asn Leu
            730                 735                 740 cca ggc ttc tct gag gca ttc cac tgc cca cga ggc agc ccc atg cac    2551
Pro Gly Phe Ser Glu Ala Phe His Cys Pro Arg Gly Ser Pro Met His
            745                 750                 755 ccc atg aag cga tgt cgc atc tgg tagccaaggc tgagctatgc tgcggccac    2605
Pro Met Lys Arg Cys Arg Ile Trp
            760                 765 gccccgccac ccagaggtcg cgaatggtgt agctggcaga gatgtgcagg tctttgcctg   2665
aaggccaccg gagccaccag ccagccctcc gcgcccagcc tagagtgtag ccaccgccc    2725 acacccggga tgagtggtgc cggtcctgcg ccccctcagg ccagtgaggg tcagcagccc   2785
aggaagagca gtcagctgcc ttccaccctc tccatagtgt gtggctaaat gttctcgagc   2845
ttcagacttg agctaagtaa acgcttcaaa gaagacaaaa aaaaaaa                 2892

<210> SEQ ID NO 4
<211> LENGTH: 2823
<212> TYPE: DNA
<213> ORGANISM: Mus musculus

<400> SEQUENCE: 4
ccggagccca ccttggccag ctcaccccaa ctctgagaca tcccaaccta gcctttaagg     60
acttgcctag aagtgactga gagcaccagg gtcccctggg cacttggggc acagcttaca    120
gcattgagag cagagaccag gacagtgcac cagcttcagt gtgtcctagg catccgatcc    180
gggctccagc tgcctctctc ctagccctgg cctgggggc ttagcggtgt gccttccacc     240
cagaaccggc tgatagggaa agtctgagag cccagtgggg atg gtg gag aga gca     295
                                              Met Val Glu Arg Ala
                                              1               5 ggc tgg tgt cgg aag aag tcc cca ggc ttc gtg gag tat ggg ctg atg     343
Gly Trp Cys Arg Lys Lys Ser Pro Gly Phe Val Glu Tyr Gly Leu Met
                10                  15                  20 gtg ctg ctg ctg ctg ttg ctg gga gcc ata gtg act ctg ggt gtc ttc     391
Val Leu Leu Leu Leu Leu Leu Gly Ala Ile Val Thr Leu Gly Val Phe
            25                  30                  35 tac agc ata gcc ctc agg gat tca tca ctg aaa agt gac atc tgc acc     439
Tyr Ser Ile Ala Leu Arg Asp Ser Ser Leu Lys Ser Asp Ile Cys Thr
        40                  45                  50 acc cca agc tgt gtg ata gca gct gcc aga atc ctc gaa aac atg gac    487
Thr Pro Ser Cys Val Ile Ala Ala Ala Arg Ile Leu Glu Asn Met Asp
    55                  60                  65 caa tcg agg aac ccc tgt gaa aac ttc tac cag tac gcc tgc gga ggc    535
Gln Ser Arg Asn Pro Cys Glu Asn Phe Tyr Gln Tyr Ala Cys Gly Gly
70                  75                  80                  85 tgg ctg agg cac cac gtg atc cca gag acc aac tcc cga tac agc gtc    583
Trp Leu Arg His His Val Ile Pro Glu Thr Asn Ser Arg Tyr Ser Val
                90                  95                  100 ttt gac atc ctg cgg gac gag ctg gag gtt atc ctc aaa ggg gtg ctg    631
Phe Asp Ile Leu Arg Asp Glu Leu Glu Val Ile Leu Lys Gly Val Leu
            105                 110                 115 gag gat tcc act tcc cag cat cgc ccg gcc gtg gag aag gcc aag aca    679
Glu Asp Ser Thr Ser Gln His Arg Pro Ala Val Glu Lys Ala Lys Thr
        120                 125                 130 cta tat cgc tcc tgc atg aac caa agt gtg atc gag aag aga gac tct    727
Leu Tyr Arg Ser Cys Met Asn Gln Ser Val Ile Glu Lys Arg Asp Ser
    135                 140                 145 gag ccc ctg ctg agc gtc tta aaa atg gta gga ggt tgg cct gtg gca    775
Glu Pro Leu Leu Ser Val Leu Lys Met Val Gly Gly Trp Pro Val Ala
```

```
            150                 155                 160                 165 ttg gat aag tgg aac gag acc atg ggc ctc aag tgg gaa ctg gag cga            823
Leu Asp Lys Trp Asn Glu Thr Met Gly Leu Lys Trp Glu Leu Glu Arg
                        170                 175                 180 cag ttg gct gtg ttg aac tcg cag ttc aac agg cgg gtc ctc atc gac            871
Gln Leu Ala Val Leu Asn Ser Gln Phe Asn Arg Arg Val Leu Ile Asp
                185                 190                 195 ctc ttc atc tgg aat gac gac cag aac tcc agc cgg cat gtc atc tac            919
Leu Phe Ile Trp Asn Asp Asp Gln Asn Ser Ser Arg His Val Ile Tyr
            200                 205                 210 ata gac cag ccc acc ttg ggc atg cca tcc cgg gag tac tat ttc cag            967
Ile Asp Gln Pro Thr Leu Gly Met Pro Ser Arg Glu Tyr Tyr Phe Gln
        215                 220                 225 gag gac aac aac cac aag gta cgg aaa gcc tac ccg gag ttc atg acg           1015
Glu Asp Asn Asn His Lys Val Arg Lys Ala Tyr Pro Glu Phe Met Thr
230                 235                 240                 245 tca gtg gcc act atg ctt agg aaa gac cag aac ctg tcc aag gag agc           1063
Ser Val Ala Thr Met Leu Arg Lys Asp Gln Asn Leu Ser Lys Glu Ser
                    250                 255                 260 gcc atg gtg cgg gag gag atg gcg gag gtg ctg gaa ctg gag acg cat           1111
Ala Met Val Arg Glu Glu Met Ala Glu Val Leu Glu Leu Glu Thr His
                265                 270                 275 ctg gcc aac gcc aca gtc ccc cag gag aaa agg cat gat gtc act gcc           1159
Leu Ala Asn Ala Thr Val Pro Gln Glu Lys Arg His Asp Val Thr Ala
            280                 285                 290 ctg tac cac cga atg gac ctg atg gag cta cag gaa agg ttt ggt ctg           1207
Leu Tyr His Arg Met Asp Leu Met Glu Leu Gln Glu Arg Phe Gly Leu
        295                 300                 305 aag ggg ttt aac tgg act ctc ttc ata caa aac gtg ttg tct tct gtg           1255
Lys Gly Phe Asn Trp Thr Leu Phe Ile Gln Asn Val Leu Ser Ser Val
310                 315                 320                 325 gaa gtc gag ctg ttc cca gat gag gag gtg gtg gtc tac ggc atc ccc           1303
Glu Val Glu Leu Phe Pro Asp Glu Glu Val Val Val Tyr Gly Ile Pro
                    330                 335                 340 tac ctg gag aat ctg gag gat atc att gat agc tac tca gca cgg acc           1351
Tyr Leu Glu Asn Leu Glu Asp Ile Ile Asp Ser Tyr Ser Ala Arg Thr
                345                 350                 355 atg cag aac tac ctg gta tgg cgc ctg gtg cta gat cga att ggc agc           1399
Met Gln Asn Tyr Leu Val Trp Arg Leu Val Leu Asp Arg Ile Gly Ser
            360                 365                 370 ctg agc cag aga ttc aaa gag gcg cgt gtg gac tac cgc aag gcg ctg           1447
Leu Ser Gln Arg Phe Lys Glu Ala Arg Val Asp Tyr Arg Lys Ala Leu
        375                 380                 385 tac ggc acg acc gtg gag gag gta cgc tgg cga gag tgt gtc agc tat           1495
Tyr Gly Thr Thr Val Glu Glu Val Arg Trp Arg Glu Cys Val Ser Tyr
390                 395                 400                 405 gtc aac agt aac atg gag agc gcc gtg ggc tcc ctc tac atc aag cgg           1543
Val Asn Ser Asn Met Glu Ser Ala Val Gly Ser Leu Tyr Ile Lys Arg
                    410                 415                 420 gcc ttc tcc aag gac agc aag agc acg tcc aga gag ctg att gag aag           1591
Ala Phe Ser Lys Asp Ser Lys Ser Thr Val Arg Glu Leu Ile Glu Lys
                425                 430                 435 ata agg tcc gtg ttt gtg gat aac ctg gat gag ctg aac tgg atg gac           1639
Ile Arg Ser Val Phe Val Asp Asn Leu Asp Glu Leu Asn Trp Met Asp
            440                 445                 450 gag gaa tcc aag aag aag gcc cag gaa aag gcc atg aat ata cgg gaa           1687
Glu Glu Ser Lys Lys Lys Ala Gln Glu Lys Ala Met Asn Ile Arg Glu
        455                 460                 465 cag att ggc tac cct gac tac att ttg gaa gat aac aat aaa cac ctg           1735
```

```
Gln Ile Gly Tyr Pro Asp Tyr Ile Leu Glu Asp Asn Asn Lys His Leu
470                 475                 480                 485 gat gag gaa tac tcc agt ttg act ttc tat gag gac ctg tat ttt gag      1783
Asp Glu Glu Tyr Ser Ser Leu Thr Phe Tyr Glu Asp Leu Tyr Phe Glu
                490                 495                 500 aac gga ctt cag aac ctc aag aac aat gcc cag agg agc ctc aag aag      1831
Asn Gly Leu Gln Asn Leu Lys Asn Asn Ala Gln Arg Ser Leu Lys Lys
                505                 510                 515 ctt cgg gaa aag gtg gac cag aat ctc tgg atc atc ggg gct gca gtg      1879
Leu Arg Glu Lys Val Asp Gln Asn Leu Trp Ile Ile Gly Ala Ala Val
            520                 525                 530 gtc aat gca ttc tac tcc cca aac aga aac cag atc gtc ttt cca gca      1927
Val Asn Ala Phe Tyr Ser Pro Asn Arg Asn Gln Ile Val Phe Pro Ala
        535                 540                 545 ggg att ctc cag ccg ccc ttc ttc agc aag gac caa cca cag tcc ttg      1975
Gly Ile Leu Gln Pro Pro Phe Phe Ser Lys Asp Gln Pro Gln Ser Leu
550                 555                 560                 565 aat ttt ggg ggc atc ggg atg gtg att ggg cac gag atc aca cac ggc      2023
Asn Phe Gly Gly Ile Gly Met Val Ile Gly His Glu Ile Thr His Gly
                570                 575                 580 ttt gat gat aat ggt cgt aac ttt gac aag aac ggc aac atg ctg gac      2071
Phe Asp Asp Asn Gly Arg Asn Phe Asp Lys Asn Gly Asn Met Leu Asp
                585                 590                 595 tgg tgg agt aac ttc tcg gcc cgg cac ttc caa cag cag tcg caa tgc      2119
Trp Trp Ser Asn Phe Ser Ala Arg His Phe Gln Gln Gln Ser Gln Cys
                600                 605                 610 atg atc tat cag tac ggc aac ttc tct tgg gaa cta gca gac aac cag      2167
Met Ile Tyr Gln Tyr Gly Asn Phe Ser Trp Glu Leu Ala Asp Asn Gln
        615                 620                 625 aat gtg aac gga ttc agt tcc ctc ggg gag aac att gcc gac aac gga      2215
Asn Val Asn Gly Phe Ser Ser Leu Gly Glu Asn Ile Ala Asp Asn Gly
630                 635                 640                 645 ggt gtg cga cag gca tac aag gct tac cta cgg tgg ctg gct gat ggc      2263
Gly Val Arg Gln Ala Tyr Lys Ala Tyr Leu Arg Trp Leu Ala Asp Gly
                650                 655                 660 ggc aaa gat cag cga ctg ccg gga ctg aac ctg acc tat gcc cag ctt      2311
Gly Lys Asp Gln Arg Leu Pro Gly Leu Asn Leu Thr Tyr Ala Gln Leu
                665                 670                 675 ttc ttc atc aac tat gcc cag gtg tgg tgt ggg tcc tat agg ccg gag      2359
Phe Phe Ile Asn Tyr Ala Gln Val Trp Cys Gly Ser Tyr Arg Pro Glu
            680                 685                 690 ttc gcc gtc cag tcc atc aag acg gac gtc cac agt cct ctt aag tac      2407
Phe Ala Val Gln Ser Ile Lys Thr Asp Val His Ser Pro Leu Lys Tyr
        695                 700                 705 agg gtg ctg ggc tca cta cag aac ctg cca ggc ttc tct gag gca ttc      2455
Arg Val Leu Gly Ser Leu Gln Asn Leu Pro Gly Phe Ser Glu Ala Phe
710                 715                 720                 725 cac tgc cca cga ggc agc ccc atg cac ccc atg aag cga tgt cgc atc      2503
His Cys Pro Arg Gly Ser Pro Met His Pro Met Lys Arg Cys Arg Ile
                730                 735                 740 tgg                                                                  2556
Trp tagccaaggc tgagctatgc tgcggccac gccccgccac ccagaggtcg cgaatggtgt agctggcaga gatgtgcagg tctttgcctg aaggccaccg gagccaccag    2616
ccagccctcc gcgcccagcc tagagtgtag ccacccgccc acacccggga tgagtggtgc    2676
cggtcctgcg cccctcagg ccagtgaggg tcagcagccc aggaagagca gtcagctgcc     2736
ttccaccctc tccatagtgt gtggctaaat gttctcgagc ttcagacttg agctaagtaa    2796
acgcttcaaa gaagacaaaa aaaaaaa                                        2823
```

```
<210> SEQ ID NO 5
<211> LENGTH: 25
<212> TYPE: DNA
<213> ORGANISM: Mus musculus

<400> SEQUENCE: 5
tcaggtccat tcggtggtac agggc                                    25

<210> SEQ ID NO 6
<211> LENGTH: 25
<212> TYPE: DNA
<213> ORGANISM: Mus musculus

<400> SEQUENCE: 6
gacatcatgc cttttctcct ggggg                                    25

<210> SEQ ID NO 7
<211> LENGTH: 25
<212> TYPE: DNA
<213> ORGANISM: Mus musculus

<400> SEQUENCE: 7
actcccggga tggcatgccc aagt                                     25

<210> SEQ ID NO 8
<211> LENGTH: 25
<212> TYPE: DNA
<213> ORGANISM: Mus musculus

<400> SEQUENCE: 8
gggagccata gtgactctgg gtgtc                                    25

<210> SEQ ID NO 9
<211> LENGTH: 25
<212> TYPE: DNA
<213> ORGANISM: Mus musculus

<400> SEQUENCE: 9
gctatcacac agcttggggt ggtgc                                    25
```

MEMBRANE-BOUND METALLOPROTEASE AND SOLUBLE SECRETED FORM THEREOF

FIELD OF THE INVENTION

The present invention relates to a novel membrane-bound metalloprotease, soluble secreted form protein thereof, DNAs encoding the proteins, and medicaments based thereon.

BACKGROUND OF THE INVENTION

Infiltration and metastasis of cancer cells accompanies destruction of related tissues. It has been shown that a variety of proteases are involved in the process. Therefore, inhibitors of metalloproteases are potential candidate compounds for carcinostatics and anti-metastatic agents.

On the other hand, there are a group of disorders characterized by abnormal structural alteration of proteins, which are caused by protease-resistant deposits of proteins of beta-sheet structure formed as a result of alteration in the folding process of proteins, such as spongiform encephalopathy, Alzheimer's disease, familial amyloidosis, sickle cell anemia, pulmonary emphysema, cirrhosis, platelet thrombosis, vascular edema and the like. They are called "conformational diseases". It is known that in various conformational diseases, there are many cases in which proteins of the proteolytic system such as protease inhibitors undergo conformational changes and accumulate. Proteases with relatively low substrate specificity and having ability to decompose denatured proteins at their early stages, therefore, would have potential to become agents for prophylaxis or treatment of those diseases.

A wide variety of biologically active peptide hormones, regulatory peptides and neuropeptides have been shown to be proteolytically activated or inactivated by members of zinc metalloproteases [Hooper, N. M., FEBS Lett., 354:1–6 (1994)]. One such class of zinc metalloproteases, represented by neutral endopeptidase 24.11 (NEP) and endothelin-converting enzyme (ECE), has recently been highlighted because of their implications in some disease states and should thus provide plausible therapeutic targets for certain diseases [Yanagisawa, M., Circulation, 89:1320–1322(1994); Turner, A. J. et al., Biochem. Pharmacol., 51:91–102(1996); Turner, A. J. et al., FASEB J., 11:355–364(1997)]. In mammals, six members of this metalloprotease family have been identified; NEP; Kell blood group antigen (KELL); ECE-1 and ECE-2; PEX, which has been associated with X-linked hypophosphatemic rickets; and a recently identified peptidase, XCE. All these members are type II membrane proteins containing a highly conserved consensus sequence of a zinc-binding motif, HEXXH (where X represents any amino acid), in their extracellular C-terminal domain. Despite the apparent structural similarity among the members of this family, a large diversity of physiological functions exists.

NEP, which is especially abundant in kidney and brain, is also expressed in various tissues as an ectoenzyme that can degrade many circulating small peptide mediators, such as enkephalins, atrial natriuretic peptide (ANP), tachykinins, and endothelins (ETs) [Roques, B. P. et al., Pharmacol. Rev., 45:87–146(1993)]. NEP is also known as the common acute lymphoblastic leukemia antigen, and its presence on leukemic cells has been associated with a better prognosis. Although the physiological substrates of NEP are still unknown, targeted disruption of the NEP gene in mice caused a dramatic sensitivity to endotoxin shock, suggesting that NEP may provide an unexpected protective role against endotoxin shock [Lu, B. et al., J. Exp. Med., 181:2271–2275 (1995)]. Moreover, in vivo pharmacological inhibition of NEP has led to a decrease in blood pressure, and NEP-deficient mice were noted to have lower mean blood pressure levels than wild-type littermates, thus indicating that NEP may also play an important role in blood pressure regulation [Lu, B. et al., Nat. Med., 3:901–907(1997)].

ECE, another well characterized member of this metalloprotease family, is involved in the regulation of vascular tone, as well as in the development of some sets of neural crest cells [Turner, A. J. et al., Biochem. Pharmacol., 51:91–102(1996); Turner, A. J. et al., FASEB J., 11:355–364 (1997)]. It converts the inactive ET precursors (big ETs) into biologically active ETs via a specific cleavage at $Trp^{21}$-Val/$Ile^{22}$ [Yanagisawa, M. et al, Nature, 332:411–415(1988); Xu, D. et al., Cell, 78: 473–485(1994)]. ECE constitutes a potential regulatory site for the production of the active peptide. Two isozymes of ECE, ECE-1 and ECE-2, have been molecularly identified and make up a subfamily within this group of type II membrane-bound metalloproteases [Xu, D. et al., Cell, 78:473–485(1994); Emoto, N. et al., J. Biol. Chem., 270:15262–15268(1995)]. Both enzymes have been shown to cleave big ET-1 to produce ET-1 with a similar overall profile of inhibitor sensitivity in vitro as well as in transfected cells. However, ECE-1 and ECE-2 exhibit the following striking differences: (i) ECE-1 cleaves big ETs in neutral pH, whereas ECE-2 functions in an acidic pH range, (ii) the sensitivity of ECE-1 to phosphoramidon is 250-fold lower than that of ECE-2 and (iii) ECE-1 is abundantly expressed in endothelial cells and other cell types known to produce mature ET-1, whereas ECE-2 mRNA is detected in neural tissues including the cerebral cortex, the cerebellum, and the adrenal medulla. Targeted disruption of the ECE-1 gene in mice revealed that ECE-1 is the physiologically relevant enzyme needed to produce active ET-1 [Yanagisawa, H. et al., Development, 125:825–836(1998)]. The physiological function of ECE-2 has not yet been elucidated.

The physiological substrates of the three other mammalian peptidases, KELL, PEX, and XCE, are still unknown. KELL, expressed on human red cells and other cell types, carries the epitopes for the KELL minor blood group antigen. Although the KELL blood group antigen is clinically important, its actual protease activity has yet to be described. The PEX gene was identified by positional cloning as a candidate gene for X-linked hypophosphatemic rickets, a dominant disorder characterized by impaired phosphate uptake in the kidney. XCE was recently isolated by screening EST date base with the ECE-1 sequence. No protease activity for XCE has been detected, hence, its physiological significance is unknown.

Recent gene targeting studies of ECE revealed that ECE-1 is a bona fide activating protease for big ET-1 and big ET-3 at specific developmental stages [Yanagisawa, H. et al., Development, 125:825–836(1998)]. However, despite the absence of ECE-1 (which resulted in craniofacial and cardiovascular defects), a significant amount of mature ET-1 peptide was still found in ECE-$1^{-/-}$ embryos, suggesting that other proteases can activate ET-1.

Upon the above-described background, the present inventors attempted to find out enzymes structurally relating to the metalloprotease family. The present inventors, as a result, successfully isolated a novel enzyme, termed soluble secreted endopeptidase (SEP), and its membrane bound form $SEP^{\Delta}$, which lacks part of its amino acids, by degenerate PCR using cDNA prepared from ECE-1$^{-/-}$ embryos as template. SEP and SEP$^\Delta$ polypeptides are identical with each other except for the 23 amino acids characteristic of SEP. Its DNA sequence predicts that SEP is a type II membrane-bound metalloprotease structurally related to NEP, ECE-1, and ECE-2. Transfection of the SEP cDNA into Chinese hamster ovary (CHO) cells resulted in the occurrence of SEP protein not only in the membrane fraction of the cells but also in the supernatant, suggesting that these cells release soluble forms of the enzyme through proper secretory machinery. Enzymological analysis of the recombinant soluble SEP protein revealed that SEP hydrolyzes a variety of peptides, which are known as substrates of NEP and/or ECE, including big ET-1, ET-1, angiotensin 1, ANP, bradykinin, and substance P. This suggest that SEP is likely a novel member of this metalloprotease family and may be involved in the metabolism of biologically active peptides.

SUMMARY OF THE INVENTION

Thus, the present invention provides proteins (SEP and SEP$^\Delta$, respectively) and salts thereof having amino acid sequences set forth under SEQ ID NO:1 and NO:2, respectively, in the Sequence Listing.

The present invention further provides metalloprotease proteins and salts thereof having a neutral optimal pH and having amino acid sequences substantially the same as the amino acid sequence set forth under SEQ ID NO:1 or NO:2 in the Sequence Listing, and which has an activity to hydrolyze endothelin 1, atrial natriuretic peptide and angiotensin I and are inhibited by 1,10-phenanthroline, phosphoramidon and thiorphan.

The present invention further provides DNAs having nucleotide sequences encoding the above-identified proteins.

The present invention further provides, in particular, DNA having the coding region nucleotide sequences of SEQ ID NO:3 or NO:4 in the Sequence Listing.

The present invention further provides DNAs having nucleotide sequences with one or more nucleotides deleted, substituted, inserted or added relative to the coding region nucleotide of SEQ ID NO:3 or NO:4 in the Sequence Listing and encoding proteins which are substantially the same as the protein encoded by the nucleotide sequence set forth under SEQ ID NO:3 or NO:4 in the Sequence Listing.

The present invention further provides DNAs comprising a nucleotide sequence which hybridize under a high-stringent condition with the DNAs having the coding region nucleotide sequences of SEQ ID NO:3 or NO:4 in the Sequence Listing.

The present invention further provides expression vectors in which on of the above-identified DNAs is incorporated.

The present invention further provides transformant cells which carry one of the above-identified vectors.

The present invention further provides a method for producing proteins or salts thereof which comprises introducing into a host cell a recombinant vector in which one of the above-identified DNAs is incorporated to form a transformant, culturing the transformant to produce a protein encoded by the one of the above DNAs, and collecting the protein.

The present invention further provide an antibody directed to the above-identified protein or peptide.

The present invention further provides pharmaceutical compositions for treatment or prophylaxis of a disease selected from the group consisting of spongiform encephalopathy, Alzheimer's disease, familial amyloidosis, sickle cell anemia, pulmonary emphysema, cirrhosis, platelet thrombosis and vascular edema, which compositions comprise one of the above-identified proteins or a salt thereof.

The present invention further provides a screening kit for selection of carcinostatics and anti-metastatic agents, said kit comprising one of the above proteins, a substrate for protease activity of the protein and a buffering agent which are enclosed separately from each other, with which kit screening is conducted based on the measurement of inhibition of protease activity of the protein by given candidate compounds.

The present invention further provides use of one of the above proteins for the manufacture of a medicament for treatment or prophylaxis of a disease selected from the group consisting of spongiform encephalopathy, Alzheimer's disease, familial amyloidosis, sickle cell, anemia, pulmonary emphysema, cirrhosis, platelet thrombosis and vascular edema.

The present invention further provides use of one of the above proteins in combination with a substrate for protease activity of the protein for the manufacture of a screening kit for selection of carcinostatics and anti-metastatic agents, with which kit screening is conducted based on the measurement of inhibition of protease activity of the protein by given candidate compounds

DETAILED DESCRIPTION OF THE INVENTION

Figure 1:
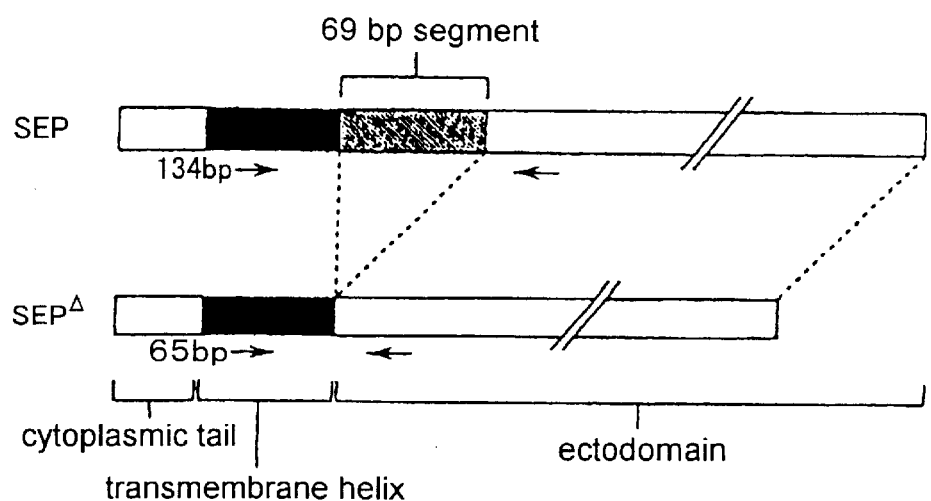
FIG. 1 illustrates sequence structures of SEP and SEP$^\Delta$.

In the present invention, a "salt" of a protein according to the present invention may be any salt that does not irreversibly denature the property and function of the protein and is physiologically and pharmaceutically acceptable. Such a salt may be an inorganic salt such as a hydrochloride, a phosphate and the like, as well as an organic salt such as an acetate, a citrate and the like. Such a variety of salts may be obtained by purifying the protein from its solution containing the conjugate base of the respective acids.

In the present invention, an "amino acid sequence substantially the same" as the amino acid sequence set forth under SEQ ID NO:1 or NO:2 in the Sequence Listing means an amino acid sequence partially altered by deletion, addition, substitution or the like of one or more amino acids and whose enzymatic activity is not substantially affected by the alteration. Such an "amino acid sequence substantially the same" may be, for example, one of those prepared by cleaving the original sequence at a site distant from its activity center, one of those prepared by replacing one or more amino acids of the original sequence with amino acids having similar chemical properties, or one of those prepared by adding to an end of the original sequence an amino acid or an amino acid sequence which do not affect the original enzymatic activity. An "amino acid sequence substantially the same" is an amino acid sequence in which preferably at least 90%, and particularly preferably no less than 95%, of the respective sequence set forth under SEQ ID NO:1 or NO:2 in the Sequence Listing is retained.

In the present invention, "having a neutral optimal pH" means having an optimal pH in the range of 6.5–8.

In the present invention, a variety of DNAs having nucleotide sequences encoding a protein having the amino acid sequence set forth under SEQ ID NO:1 or NO:2 can be easily prepared based on the knowledge on degeneracy of the genetic code.

In the present invention, "one or more" nucleotides in the phrase "one or more nucleotides deleted, substituted, inserted or added" are generally a few (e.g., 3 or 4) to ten nucleotides.

In the present invention, "encoding substantially same proteins" as the protein encoded by the nucleotide sequences set forth under SEQ ID NO:3 or NO:4 means encoding metalloprotease proteins comparable to the protein encoded by the nucleotide sequences set forth under SEQ ID NO:3 or NO:4 with respect to its optimal pH, hydrolyzing activity on endothelin I, on atrial natriuretic peptide and on angiotensin I, as well as with respect to inhibition by 1,10-phenanthroline, phosphoramidon and thiorphan.

In the specification, an example of "high-stringent conditions" is a condition in which the concentration of sodium ion is about 19–40 mM, preferably about 19–20 mM and the temperature is about 50–70° C., preferably about 60–65° C. Most preferable is a condition in which the concentration of sodium ion is about 19 mM and the temperature is about 65° C.

A variety of mutants are available using recombinant DNA technology. First, a mutation can be introduced into a DNA clone fragment through different chemical and enzymatic processes, and the mutant DNAs thus obtained are then sequenced to select particular mutants with intended merits. This method allows a systematic preparation of different mutants regardless of their phenotypes. General methods of preparing a mutant clone DNA are as follows:

1. With the help of an oligonucleotide, substitution, deletion, insertion or addition can be directly carried out in a given DNA sequence. This method enables to introduce a number of mutations in a small region of a DNA.
2. Using a longer oligonucleotide, it is possible to synthesize a desired gene.
3. By means of region-specific mutagenesis, a desired mutation can be introduced into a large (1–3 kb) DNA region.
4. Linker-scanning mutagenesis of DNA is a method suited for introducing a cluster point mutation into a relatively small (4–10 bp) DNA region
5. PCR is also utilized as a method for direct introduction of a mutation. [References: Current Protocols in Molecular Biology., 3 Vols., Edited by Ausubel F. M. et al., John Wiley & Sons, Inc., Current Protocols., Vol. 1, Chapter 8: Mutagenesis of Cloned DNA, pages 8.0.1–8.5.10]

Also well known to those skilled in the art are methods of preparing plasmids and vectors which can express proteins encoded by those DNAs. That is, by inserting a DNA carrying a desired gene into a expression vector DNA using a combination of restriction enzymes and a ligase, a recombinant plasmid is readily constructed which carries the desired gene. The recombinant plasmid thus obtained is then introduced into different cells to transfect them, thereby producing transformed cells. Cells which may be utilized range from prokaryotic cells, e.g. E. coli, to eukaryotic cells, e.g., yeast, insect, plant and animal cells. In the present invention, "transformant cells" include any of these prokaryotic and eukaryotic cells. [References: Vectors Essential Data. Gacesa P. and Ramji D. P., 166 pages. BIOS Scientific Publishers Limited 1994., John Wiley & Sons in association with BIOS Scientific Publishers Ltd. Expression vectors, pages 9–12.]

Introduction of a recombinant plasmid into host cells is effected by calcium chloride method or electroporation. Calcium chloride method provides efficient transformation and requires no special apparatus. For higher efficiency, electroporation is recommended.

Introduction of a recombinant plasmid into host cells is effected by calcium chloride method or electroporation. Calcium chloride method provides efficient transformation and requires no special apparatus. For higher efficiency, electroporation is recommended.

Two types of transfection are known which are generally carried out on animal cell lines, i.e., transient and permanent types. In transient transfection, transformed cells are cultured for 1–4 days to effect transcription and replication of the transfected gene, and then the cells are harvested and their DNA analyzed. Alternatively, in many studies, a stable transformant cell line is produced, in which the transfected gene is incorporated into the chromosomes. Examples of the method for transfection include calcium phosphate method, electroporation, and liposome fusion method.

Two types of transfection are known which are generally carried out on animal cell lines, i.e., transient: and permanent types. In transient transfection, transformed cells are cultured for 1–4 days to effect transcription and replication of the transfected gene, and then the cells are harvested and their DNA analyzed. Alternatively, in many studies, a stable transformant cell line is produced, in which the transfected gene is incorporated into the chromosomes. Examples of the method for transfection include calcium phosphate method, electroporation, and liposome fusion method.

Polyclonal and monoclonal antibodies directed to the proteins of the present invention can readily be prepared using techniques well known in the art. Antibodies thus prepared may be used as laboratory reagents and diagnostic agents for diseases associated with the gene of the present invention. The antibodies obtained are also used for preparation of antibody columns, for immunoprecipitation as well as for identification of the antigen by Western blotting.

A general method for preparing a monoclonal antibody in mg-scale directed to the proteins of the present invention is as follows: Mice are inoculated with the antigen protein to immunize, and the spleen is removed from the mice which exhibit a sufficient antibody titer. The spleen cells are separated, and B cells are selected and fused with myeloma cells of B cell origin to form hybridoma cells which secrete the antibody. The monoclonal antibody secreted from the hybridoma cells is purified from the culture medium by means of an affinity column, ion-exchange, or gel filtration, etc. The polyclonal antibody of the present invention also may be prepared by a conventional method: Using rabbits, horses, mice or guinea pigs as animals to be immunized, the antigen protein is inoculated along one of the schedules well known in the art to immunize the animals, and then IgG, etc. are isolated from the collected serum. [Reference: Current Protocols in Molecular Biology, 3 vols. Edited by Ausubel F. M. et al., John Wiley & Sons, Inc., Current Protocols, Vol. 2, Chapter 11: Immunology, pages 11.0.1–11.16.13.]

The protein according to the present invention has relatively low substrate specificity and hydrolyzes a wide range of substrates. Therefore, the protein is expected to hydrolyze denatured proteins or regulate proteins of proteolytic system, in early stages of so-called conformational diseases, thereby preventing accumulation of protease-resistant deposits. The composition of the present invention may be in the form of an injection, for example, which may contain ingredients usually employed in injections such as buffering agents, stabilizers, isotonizers, etc.

In a kit comprising one of the proteins according to the invention and its substrate, big ET-1, for example, may be used as the substrate. As a buffering agent, 0.1 M MES-NaOH containing 0.5 M NaCl (pH 7.4), for example, may be used. The reaction is allowed by incubation preferably at 37° C. for 1–2 hrs. The reaction is terminated by addition of 10 $\mu$l of 10 mM EDTA per 0.5 ml of the reaction mixture.

One class of zinc metalloproteases, represented by neutral endopeptidase 24.11 and endothelin-converting enzyme, has been shown to be involved in proteolytic activation or inactivation of many regulatory peptides. The present inventors performed molecular cloning and characterization of a novel member of this type II membrane-bound metalloprotease family, termed soluble secreted endopeptidase (SEP). Alternative splicing results in the generation of another transcript, $SEP^\Delta$, which lacks a 69-base pair nucleotide segment, which corresponds to SEP amino acid residues 41–63, following the transmembrane helix. Both SEP and $SEP^\Delta$ mRNAs are detected in all mouse tissues examined. Transfection of an SEP cDNA expression construct resulted in the expression of the memrbrane-bound form of SEP in the early secretory pathway as well as the soluble secreted form of the enzyme in the culture medium. In contrast, transfection of the $SEP^\Delta$ cDNA only resulted in the expression of the membrane-bound form. In vitro enzymological analysis of the recombinant soluble form of SEP demonstrated that it hydrolyzes a variety of vasoactive peptides, including endothelin-1, atrial natriuretic peptide, and angiotensin I. This activity of SEP was inhibited by phosphoramidon and the neutral endopeptidase 24.11 specific inhibitor thiorphan, but it was only partially inhibited by the endothelin-converting enzyme specific inhibitor FR901533. These findings suggest that SEP is a novel metalloprotease that possesses a broad substrate specificity and that it may be involved in the metabolism of biologically active peptides intracellularly as well as extracellularly.

EXAMPLES

Experimental Procedures

Reagents: Synthetic human big ET-1(1–88), human ET-1, ANP, angiotensin 1, bradykinin, and substance P were obtained from American Peptides, Phosphoramidon, thiorphan, 1,10-phenanthroline, and captopril were obtained from Sigma. FR901533 (WS79089B) was a gift from Fujisawa Pharmaceutical Co., Ltd.

cDNA Cloning and Sequencing:

Near-term ECE-1$^{-/-}$ embryos were kindly provided by Dr. M. Yanagisawa (University of Texas Southwestern Medical Center, Dallas, Tex.). A partial cDNA clone encoding SEP was obtained by reserve transcription (RT)-PCR against whole ECE-1$^{-/-}$ embryo mRNA with degenerate primers based on the highly conserved amino acid sequences of ECE-1, ECE-2, NEP, and PEX cDNAs.

The PCR contained 60 mM Tris-Cl (pH 8.5), 15 mM ammonium sulfate, 1.5 mM magnesium chloride, 0.25 mM of each dNTP, 7.5 pmol of each degenerate primer, 5'-at(a/g/c/t) gt(a/g/c/t)tt(c/t)cc(a/g/c/t)gc(a/t)gg-3' and 5'-t(ag)tc(a/g/c/t)gc(a/g/t)at(a/g)tt(c/t)tc-3', 10 ng of first strand cDNA, and 2.5 units of Tag DNA polymerase. The initial five cycles were carried out at an annealing temperature of 37° C., and then 35 more cycles were carried out at an annealing temperature of 48° C. The PCR products were separated in a 1% agarose gel, and an approximately 300-base pair region was excised from the gel. The extracted DNA was subcloned into pT7 vector (Novagen) and sequenced. A cDNA library was constructed by using the SuperScript kit (Life Technologies, Inc.) against poly(A)$^+$RNA from mouse testis. Approximately 1×10$^6$ plaques from the unamplified library were screened with random primed $^{32}$P-labeled RT-PCR product as probe. The 5' end of the cDNA was cloned by 5'-rapid amplification of cDNA ends against the ECE-1$^{-/-}$ embryo and mouse brain. The first strand cDNA was synthesized with reverse transcriptase by using a specific primer 5'-tcaggtccattcggtggtacagggc-3' (corresponding to amino acids 293–301 of SEP). With terminal deoxynuclectidyltransferase, an oligo(dC) anchor was added to the 3' end of the first strand cDNA. The first round PCR was performed as recommended by the manufacturer with a specific 3' primer, 5'-gacatcatgccttttctcctggggg-3' (corresponding to amino acids 283–291 of SEP) and a 5' another primer. The product was then subjected to the second amplification by using a nested specific 3' primer, 5'-actcccgggatggcatgcccaaggt-3' (corresponding to amino acids 218–226 of SEP). The product of this PCF, was subcloned into pT7 vector and subsequently sequenced. For nucleotide sequencing, overlapping restriction fragments of the cDNA were subcloned into the pBluescript plasmid vector (Stratagene), and double strand plasmid DNA sequenced by a model 310 DNA Sequencer (Applied Biosystems). Both strands of cDNA were covered at least twice.

Reverse Transcription-PCR:

First strand cDNA synthesis was carried out with 5 $\mu$g of total RNA from mouse tissues and oligo(dT)$_{12-18}$ primers using SuperScript reverse transcriptase II (Life Technologies, Inc.) as recommended by the manufacturer. The PCR contained 20 mM Tris-Cl (pH 8.5), 15 mM ammonium sulfate, 1.5 mM magnesium chloride, a 0.25 mM concentration of each dNTP, a 100 nM concentration of each amplification primer, 10 ng of first strand cDNA, and 2.5 units of Taq polymerase. The primers, 5'-gggagccatagtgactctgggtgtc-3' (corresponding to amid acids 28–36 of SEP) and 5'-gctatcacacagcttggggtggtgc-3' (corresponding to amino acids 75–83 of SEP) were used for both spliceoforms of mouse SEP. The PCR products were verified by DNA sequencing.

Antibody and Immunoblotting:

Antibody directed against SEP was produced by immunizing rabbits with a synthetic peptides, CPRGSPMHPMKRCRIW, corresponding to the C-terminal 16 amino acids of mouse SEP. Rabbits were immunized with keyhole limpet hemocyanin-coupled peptides in complete adjuvant, followed by antisera preparation. Immunoblot analysis was performed with horseradish peroxidase-conjugated anti-rabbit IgG by using the ECL detection kit (Amersham Pharmacia Biotech) as recommended by the manufacturer.

Endoglycosidase Digestion:

Partially purified SEP aid the membrane preparations from CHO/SEP and CHO/SEP$^\Delta$ cells were incubated with either 1 unit of endo-$\beta$-N-acetylglucosaminidase or peptide-N-glycosidase F (Roche Molecular Biochemicals) in 50 mM sodium phosphate buffer (pH 5.5) at 37° C. for 16 h. Control sampled were incubated in parallel without endoglycosidases in the same buffer at 37° C. for 16 h. The samples were them subjected to immunoblotting.

Cell Culture and Transfection:

CHO-K1 cells were cultured [Emoto, N. et al., J. Biol. Chem., 274:1509–1518(1999)]. Double transfection of prepro-ET-1and ECE-1a, SEP, or SEP$^\Delta$ was performed using LipofectAMINE (Life Technologies, Inc.). Twelve hours after transfection, cells were refed with fresh medium. The medium was conditioned for an additional 18 h and was directly subjected to a sandwich-type enzyme immunoassay, which showed no cross-reactivity between big ET-1 and ET-1. For in vitro enzymological charactenization, an SEP expression construct was transiently transfected into CHO-K1 cells. The medium was conditioned for 48 h in CHO-SFM II (Life Technologies, Inc.) and was subjected to a wheat germ lectin column (1×1 ml HiTrap wheat germ lectin; Amersham Pharmacia Biotech) equilibrated with 20 mM Tris-Cl (pH 7.4) and 0.5M NaCl. The column was washed and eluted with the same buffer containing 0.5M N-acetylglucosamine. The active fraction was subsequently subjected to a Centriprep concentrator (Amicon).

Fluorescent Immunocytochemistry:

Cells were seeded onto coverslips and cultured for 2 days. Fluorescent immunocytochemistry was performed as follows. Briefly, for intracellular staining, cells were fixed and permeabilized in methanol for 5 min at −20° C. After washing in phosphate-buffered saline (PBS), PBS containing 10% (v/v) normal goat serum was added. Following incubation for 1 h at 37° C., the normal goat serum/PBS was replaced with a buffer containing polyclonal antibody (1:100) directed against bovine SEP C-terminal peptides. After incubation for 90 min at 37° C., the cells were washed and then incubated in normal goat serum/PBS containing 7.5 $\mu$g/ml fluorescein isothiocyanate-labeled goat anti-rabbit IgG (Zymed Laboratories Inc.). After 45 min at 37° C., the cells were extensively washed. The coverslips were mounted on microscope slides with 90% (v/v) glycerol, 50 mM Tris-HCl (pH 9.0), and 2.5% (w/v) 1.4-diazadicyclo-[2.2.2]-octane. For cell surface staining, cells were fixed in PBS containing 4% paraformaldehyde for 15 min at room temperature. Following two washes in PBS, the cells were treated with the SEP antibody and fluorescein isothiocyanate-labeled goat anti-rabbit IgG as described above. Three negative control conditions were examined: staining with preimmune serum, with antibody after preabsorption, and omission of the primary antibody. None of these conditions resulted in cell staining.

Measurement of Enzyme Activity:

Reaction mixtures for enzyme assay (100 $\mu$l) contained 0.1 M MES-NaOH(pH 7.4), 0.5 $\mu$M peptide, and an enzyme fraction. For some experiments, the reactions were preincubated at 37° C. with various protease inhibitors for 15 min prior to the addition of the peptide. The reactions were incubated at 37° C. for 1–12 h in siliconized 0.5-ml microcentrifuge tubes. The enzyme reaction was terminated by adding 1 $\mu$l of 10 mM EDTA. The mixture was then injected into a C18 reverse-phase high pressure liquid chromatography (HPLC) column ($\mu$RPC C2/C18, ST4.6/100; Amersham Pharmacia Biotech) that was equilibrated with 10% (v/v) acetonitrile and 0.1% (v/v) trifluoroacetic acid. The column was eluted at a flow rate of 1 ml/min with a 10–80% linear gradient of acetonitrile and 0.1% trifluoroacetic acid over 43 min, followed by a 100% acetonitrile for an additional 3 min. Peptides were detected by absorbance at 220 nm.

Mass Spectrometry:

Matrix-assisted laser desorption/ionization mass spectra were acquired on Voyager RP delayed extraction mass spectrometer (PerSeptive Biosystems, Inc.). Radiation from a nitrogen laser (Laser Science, Inc.)(337 nm, 3-ns pulse width) was used to desorb ions from the target. All reflector delayed extraction experiments were performed using an extraction grid voltage of 14.5 kV and a pulse delay of 225 ns.

Results

Cloning of SEP:

A pair of highly degenerate oligonucleotide primers was designed based on conserved amino acid sequences of known members of the membrane-bound metalloprotease family: ECE-1, ECE-2, NEP, and PEX. Subsequent RT-PCR from whole ECE-1$^{-/-}$ mouse embryo RNA yielded cDNA products of the predicted size. These cDNA fragments were subcloned into plasmid vectors and its nucleotide sequence determined. The sequences from randomly picked plasmid clones revealed that the 300-base pair cDNA product was a mixture of two distinct cDNA sequences: most plasmid clones encoded mouse NEP, whereas the nucleotide sequence from one clone predicted a closely related polypeptide sequence to members of this metalloprotease family. The present inventors named this novel putative metalloprotease SEP.

Figure 2:
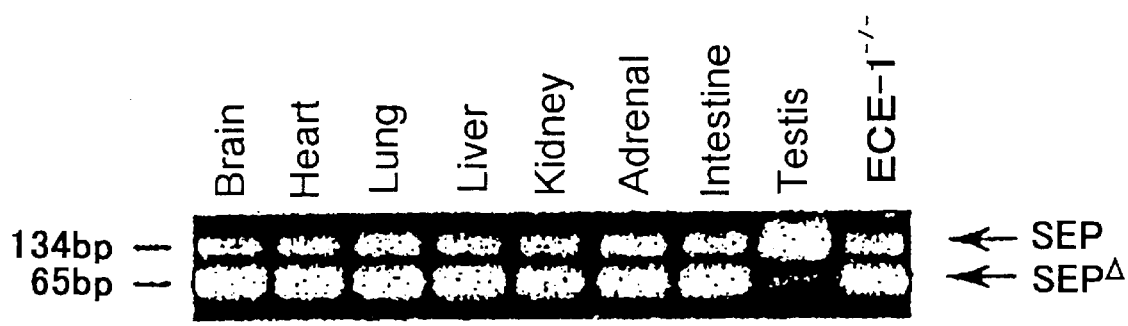
FIG. 2 shows the result of an electrophoresis of RT-PCR products showing expression of SEP and SEP$^\Delta$ in various tissues.

Using the cloned SEP RT-PCR product as a probe, the present inventors screened a mouse testis cDNA library, because SEP mRNA was most abundantly expressed in testis (see FIG. 2). Positive clones were purified and sequenced, with the overlapping nucleotide sequences of all these clones confirmed as being identical. The nucleotide sequences of the longest SEP cDNAs had a 5'-atg triplet codon that was preceded by an in-frame stop codon and followed by a long open reading frame. The encoded amino acid sequence of SEP is shown under SEQ ID NO:1 in the Sequence Listing.

While screening to isolate a full-length SEP cDNA, the present inventors performed 5'-rapid amplification of cDNA ends on RNA from ECE-1$^{-/-}$ embryo, mouse brain, and mouse testis using a nested set of specific internal primers to assess the 5' diversity of SEP mRNA. This yielded two products. The nucleotide sequence of one product was identical to the 5'-end of the full-length SEP cDNA isolated by the screening. However, the sequencing results of other clones revealed that they contained cDNA derived from SEP mRNA but lacked a 69-base pair nucleotides segment immediately following the putative transmembrane helix, presumably due to alternative splicing (FIG. 1 and SEQ ID NO:3 and NO:4). In FIG. 1, closed box represents predicted transmembrane domains, and hatched box represents a 69-base pair segment unique to SEP. Arrows represent PCR primers used to amplify the SEP and SEP$^\Delta$ cDNAs. Based on these findings, we termed this clone SEP$^\Delta$ (SEQ ID NO:4).

Structure of SEP and SEP$^\Delta$:

The SEP cDNA sequence encodes a novel 765-amino acid polypeptide, which shares important structural features with the NEP metalloprotease family [Hooper, N. M., FEBS Lett., 354:1–6(1994); Turner, A. J. et al., FASEB J., 11:355–364(1997)]. (i) The cDNA predicts a type II integral membrane protein with a 17-residue N-terminal cytoplasmic tail, a 21-residue putative transmembrane helix (i.e., amino acids 18–38 in SEQ ID NO:1 and NO:2), and a large (727 residue) extracellular C-terminal part. (ii) The extracellular portion of SEP constitutes the putative catalytic domain and contains a highly conserved consensus sequence (residues 597–605) of a zinc-binding motif, $\phi$XHE$\phi\phi$H$\phi\psi$ (where $\phi$ and $\psi$ represent an uncharged and a hydrophobic amino acids, respectively), that is shared by many metalloprotease. (iii) SEP has nine predicted sites for N-glycosylation in the extracellular domain, suggesting that SEP is a highly glycosylated protein, like NEP and ECE. (iv) There are 10 Cys residues in the extracellular domain that are conserved in all the proteins of this metalloprotease family.

A search using the Entrez sequence data base pointed out a significant similarity of the SEP sequence to NEP, ECE-1, ECE-2, XCE, and PEX. The sequence similarity is especially high within the C-terminal one-third of the putative extracellular domain, including the region around the zinc binding motif. Within this region (amino acids 511–765 of SEP), the identities of mouse SEP with respect to mouse NEP, human ECE-1, bovine ECE-2, and human ECE-1, bovine ECE-2, and human XCE are 65.1%, 47.7%, 44.5%, and 46.1%, respectively.

Tissue Distribution of SEP and SEP$^\Delta$ mRNA:

Northern blot analysis using total RNA from a variety of mouse tissues revealed relatively large amounts of 3.8-kilobase SEP mRNA in testis (date not shown). Small amounts of SEP mRNA were also expressed in the ovary. No signal was observed in other tissues, including the brain, lung, heart, liver, kidney, adrenal gland, and intestine. The present inventors then examined the expression of SEP and SEP$^\Delta$ mRNA in various mouse tissues by RT-PCR using primers to amplify both subisoforms of SEP. Two fragments corresponding to SEP and SEP$^\Delta$ (134 and 65 base pairs, respectively) were detected in all tissues examined as well as in the ECE-1$^{-/-}$ embryo (FIG. 2). Although RT-PCR is not strictly quantitative, the data suggest that SEP is the major isoform in testis, whereas SEP$^\Delta$ is predominantly expressed in other tissues.

Figure 3:
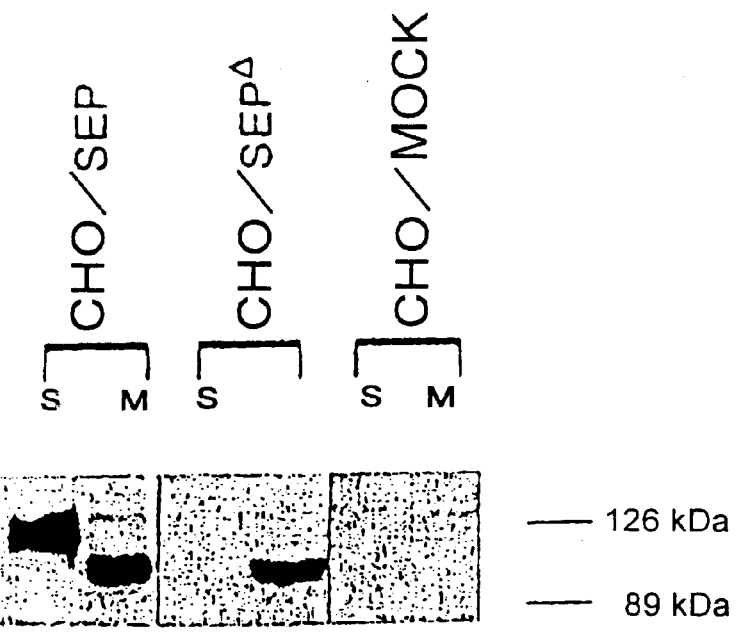
FIG. 3 shows the result of an immunoblot analysis of supernatant and membrane fractions from CHO/SEP, CHO/SEP$^\Delta$ and control cells.
Figure 4:
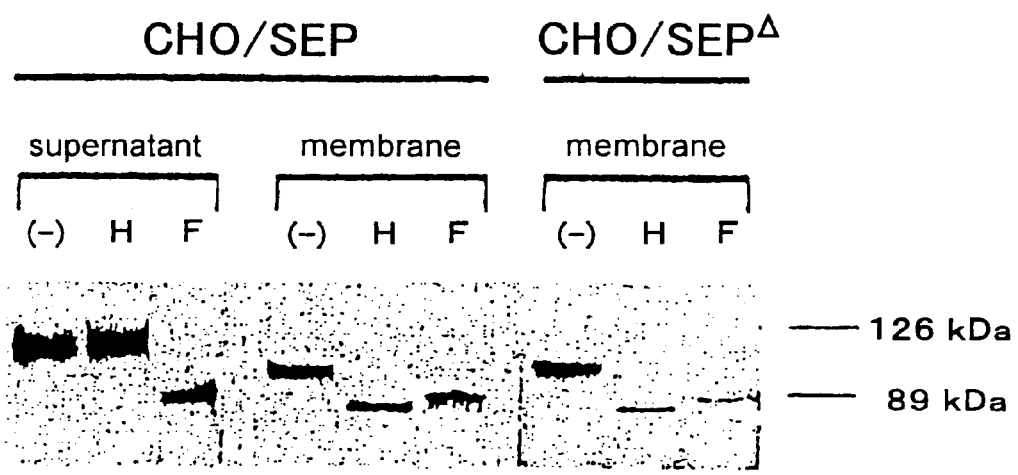
FIG. 4 shows the result of an electrophoresis after deglycosylation of soluble and membrane-bound form of SEP.

Expression of SEP in Eukaryotic Cells:

To characterize the properties of cloned SEP and SEP$^\Delta$, the present inventors generated transfectant cells, CHO/SEP and CHO/SEP$^\Delta$, by transiently transfecting expression constructs driven by the SR $\alpha$ viral promoter [Emoto, N. et al., J. Biol. Chem., 274:1509–1518(1999)]. Immunoblot analysis with an anti-SEP C-terminal peptide antiserum showed that both SEP and SEP$^\Delta$ proteins are expressed as an approximate 110-kDa protein in the membrane preparation from these cells. In addition, the present inventors detected appreciable amounts of SEP-immunoreactive material with am apparent molecular mass of approximately 126 kDa in culture medium conditioned with CHO/SEP cells, suggesting that these cells release soluble forms of SEP into the culture medium (See FIG. 3: S=supernatant fraction, M=membrane fraction: 7.5% SDS-polyacrylamide gel electrophoresis under reduced conditions). In contrast, SEP immunoreactivity was not detected in the conditioned media of both CHO/SEP$^\Delta$ and untransfected CHO cells. These observations demonstrate that CHO/SEP cells express the 110-kDa membrane-bound form of SEP as well as the 126-kDa soluble form of SEP in the medium, whereas CHO/SEP$^\Delta$ cells express only the membrane-bound form.

Because cDNA cloning of SEP revealed that it is a highly glycosylated protein, the present inventors assumed that the variation in the apparent molecular mass observed on immunoblot analysis was largely due to the presence of sugar moieties. To analyze the sugar side chains of SEP, the present inventors examined the sensitivity of both the 1-kDa membrane-bound SEP and the 126-kDa soluble forms of SEP to endo-$\beta$-N acetylglucosaminidase H (Endo H) and peptide-N-glycosidase F (PNGase F). Briefly, the soluble from of SEP in the supernatant as well as the membrane-bound SEP were incubated with Endo H (H) or PNGase F (F) as described under "Experimental Procedures". Control samples (−) were incubated in parallel without endoglycosidases using an identical buffer. The samples then were subjected to immunoblotting. Proteins containing high mannose sugar moieties, found in the early secretory pathway, including the endoplasmic reticulum and a portion of the Golgi apparatus, are sensitive to both Endo H and PNGase F. In contrast, proteins of which the sugar side chains have been further modified to complex oligosaccharides, which occur in the Golgi apparatus, are sensitive to PNGase F but resistant to Endo H. Treatment of solubilized membranes from CHO/SEP cells with either Endo H or PNGase F reduced the apparent molecular mass from 110 to 89 kDa, which corresponds to the calculated molecular mass of SEP. These observations suggest that the 110-kDa species observed in the membrane fraction of the cells is the partially glycosylated protein present in early secretory pathway. In contrast, although PNGase F treatment of the conditioned medium reduced the size from 126 to 89 kDa, Endo H had no effect on these species, indicating that the SEP protein in conditioned medium is resistant to Endo H. These observations suggest that the presence of the SEP protein in the medium is due to its secretion after complete glycosylation during transit through the Golgi apparatus. Taken together, these results suggest that CHO/SEP cells express membrane-bound SEP protein in the membrane of the compartments along the early secretory pathway in the cell and also secrete a soluble form of protein in the culture medium through proper secretory machinery.

Figure 5:
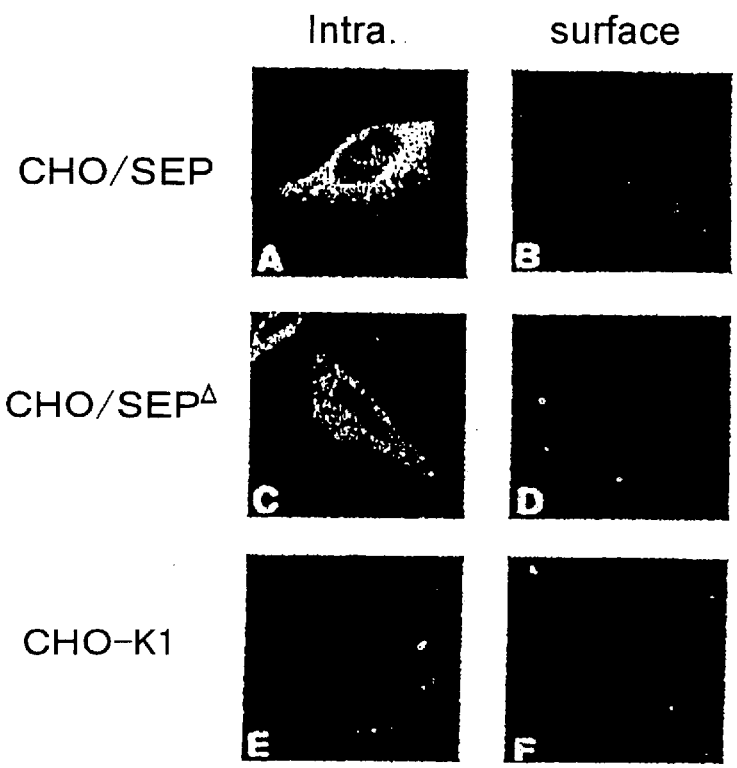
FIG. 5 shows the result of an analysis by fluorescence immunocytochemistry of CHO cells transfected with either the SEP or SEP$^\Delta$ cDNAs.

To examine the subcellular localization of membrane-bound SEP protein, the present inventors immunostained both CHO/SEP and CHO/SEP$^\Delta$ cells with antibodies that recognize the common C-terminal ectodomain of SEP. Briefly, CHO cells transfected with either the SEP or SEP$^\Delta$ expression construct were stained for intracellular (A, C, and E) or cell surface (B, D, and F) staining as described under "Experimental Procedures" (FIG. 5). Without permeabilization, both cells stained faintly, indicating that these cells expressed little SEP on the cell surface (FIG. 5, B and D). After permeabilization, both cells showed strong intracellular staining (FIG. 5, A and C). CHO-K1 cell, the parent CHO cell line, exhibited no staining (FIG. 5, E and F). These findings indicate that the membrane-bound SEP expressed in CHO cells appears to be located inside the cells, presumably in the early secretory pathway, which is compatible with its sensitivity to Endo H.

Figure 6:
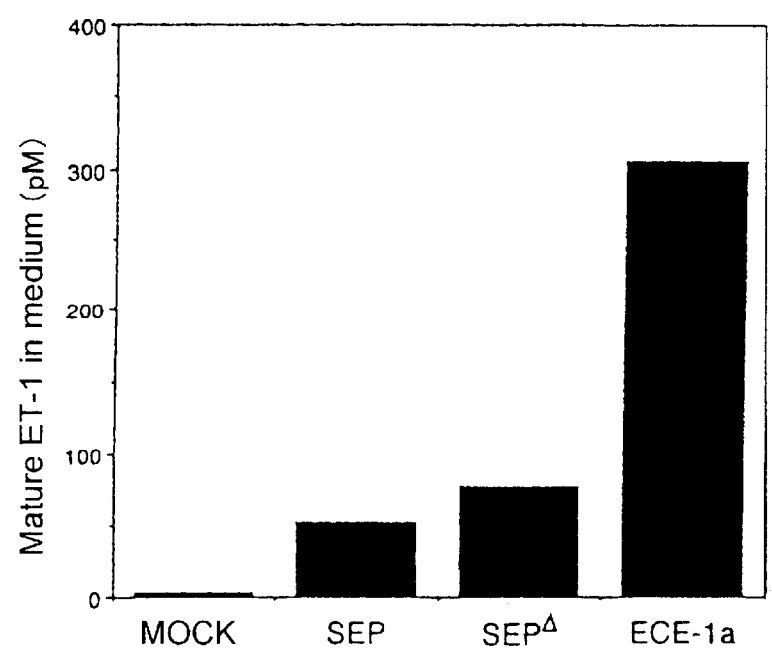
FIG. 6 is a graph showing production of mature ET-1 by CHO cells doubly transfected with prepro-ET-1 and SEP, SEP$^\Delta$ or ECE-1a cDNAs.
Figure 7:
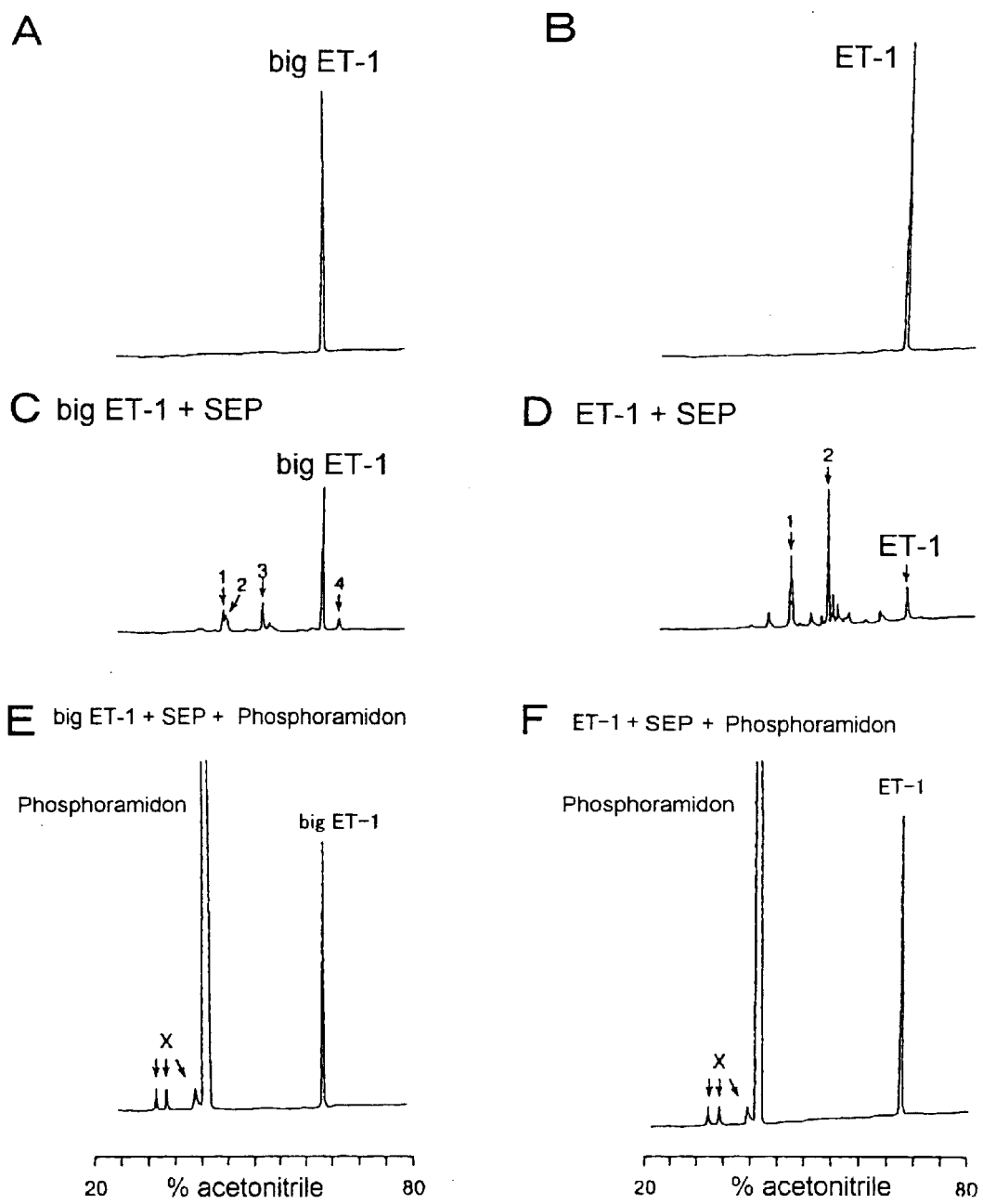
FIG. 7 shows HPLC charts showing hydrolysis of big ET-1 and ET-1 by SEP.

Cleavage of Big ET-1 by Live SEP-transfected Cells:

The present inventors first examined whether SEP can convert big ET-1 by a double transfection assay described previously [Xu, D. et al., Cell, 78: 473–485(1994); Emoto, N. et al., J. Biol. Chem.:270:15262–15268(1995); Emoto, N. et al., J. Biol. Chem., 274:1509–1518(1999)]. CHO/SEP and CHO/SEP$^\Delta$ cells were transiently transfected with a prepro-ET-1 construct, with the amount of mature ET-1 subsequently secreted from these cells into the medium determined by a sandwich-type enzyme immunoassay. As shown in FIG. 6, parental CHO cells transfected with prepro-ET-1 cDNA did not secrete a significant amount of mature ET-1, consistent with the finding that CHO cells do not have detectable ECE activity [Xu, D. et al., Cell, 78:473–485 (1994)]. On the other hand, CHO/ECE-1a cells, which constitutively express bovine ECE-1a, transfected with the prepro-ET-1 construct, produced large amounts of mature ET-1. This is also consistent with the previous finding that the ECE-1 cDNA confers the ability to secrete mature ET-1 to these cells [Xu, D. et al., Cell, 78:473–485(1994)]. CHO/SEP and CHO/SEP$^A$cells transfected with prepro-ET-1 cDNA also produced significant amounts of mature ET-1, indicating that SEP has an ability to cleave big ET-1 to produce mature ET-1. However, much smaller amounts of mature ET-1 were produced by CHO/SEP cells than those by CHO/ECE-1a cells. These observations suggest that SEP may have smaller ECE-like activity than ECE-1. Alternatively, reduced levels of ET-1 may also be due to the possibility that SEP may further degrade the ET-1 after the cleavage at the ECE-1 specific $Trp^{21}$-$Val^{22}$ cleavage site in big ET-1. Determination of Cleavage Sites of Big ET-1 and ET-1 by Recombinant Soluble SEP:

Previously, the present inventors have shown that ECE-1 cleaves the $Trp^{21}$-$Val^{22}$ bond of big ET-1 (1–38) to produce mature ET-1(1–21) and the C-terminal half of big ET-1 (22–38) without further cleaving other parts of big ET-1 or ET-1 [Xu, D. et al., Cell, 78:473–485(1994)]. To examine the cleavage site(s) of big ET-1 and mature ET-1 by recombinant SEP in an in vivo assay, the present inventors partially purified the soluble form of SEP from the conditioned medium of CHO/SEP cells. The present inventors then incubated relatively large amounts of big ET-1 (10 $\mu$M) and ET-1 (1.5 $\mu$M) with partially purified SEP for a prolonged period of time (12 h) while directly monitoring the cleavage by reverse-phase HPLC. Product peaks were collected, and the peptides were identified by mass spectrometry. Big ET-1 (1–38) was hydrolyzed to a significant degree (42%) by the soluble form of SEP, and HPLC resolved at least four distinct product peaks (FIG. 7B). Two peptides products (FIG. 7C, peaks 1 and 4) were co-eluted with the standards of big ET-1 (22–38) and mature ET-1 (1–21), respectively. Analysis using mass spectrometry confirmed that they were big ET-1 (22–38) and mature ET-1(1–2 1), with an m/z value for $(M+H)^+$ of 1810 and 2493, respectively. These finding indicate that the soluble form of SEP can produce ET-1 by cleaving at the specific $Trp^{21}$-$Val^{22}$ site of big ET-1. On the other hand, it appears that ET-1 is further digested by the soluble form of SEP. FIG. 7D shows that ET-1 was digested to near completion, with two major product peaks resolved by HPLC under these conditions, indicating that the soluble form of SEP hydrolyzes mature ET-1 at multiple sites. These two major peaks (FIG. 7D, peaks 1 and 2) from mature ET-1 were co-eluted with the peaks (FIG. 8C, peaks 2 and 3, respectively) produced from big ET-1 hydrolysis. Using molecular masses, one peptide product (FIG. 7; C, peak 3, and D, peak 2) was identified as ET-1 (1–16). Another peptide product (FIG. 7; C, peak 2, and D, peak 1) appeared to be the two-chain ET-1 (1–16), which is held together by two disulfide bonds between $Cys^1$ and $Cys^{15}$ and between $Cys^3$ and $Cys^{11}$, presumably produced by cleavage at one site between $Ser^4$ and $Glu^{10}$ of ET-1 (1–16). A parallel preparation of the protein from untransfected CHO cells exhibited no detectable activity for both big ET-1. These activities of the soluble form of SEP were completely inhibited by 100 $\mu$M phosphoramidon (FIG. 7, E and F).

These results suggest that big ET-1 is initially cleaved at the $Trp^{21}$-$Val^{22}$ site by the soluble SEP, resulting in the production of ET-1 and that the newly formed ET-1 may be concomitantly degraded by the soluble SEP.
Properties of Recombinant Soluble Form of SEP:

The present inventors next assessed the enzymological properties of cloned SEP by using its ET-1 degrading activity. This activity of soluble form of SEP was inhibited in vitro by 1,10-phenanthroline, the metalloprotease inhibitor phosphoramidon, and the specific NEP inhibitor thiorphan (See Table I).

TABLE 1

Inhibitor Profile of SEP Partially Purified from the Conditioned Medium of CHO/SEP Cells

| Inhibitor (100 $\mu$M) | SEP activity |
|---|---|
| No inhibitor | 100 |
| 1,10-Phenanthroline | 1 |
| Thiorphan | 2 |
| Phosphoramidon | 8 |
| Fr901533 | 38 |
| Captopril | 103 |

Figure 8:
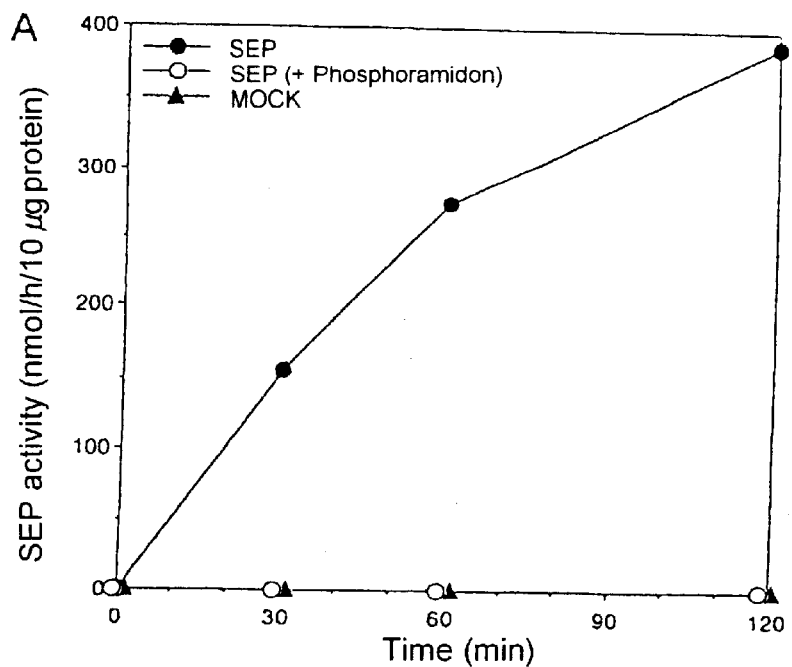
FIG. 8 is a graph showing functional expression of the SEP cDNA in transfected CHO cells.
Figure 9:
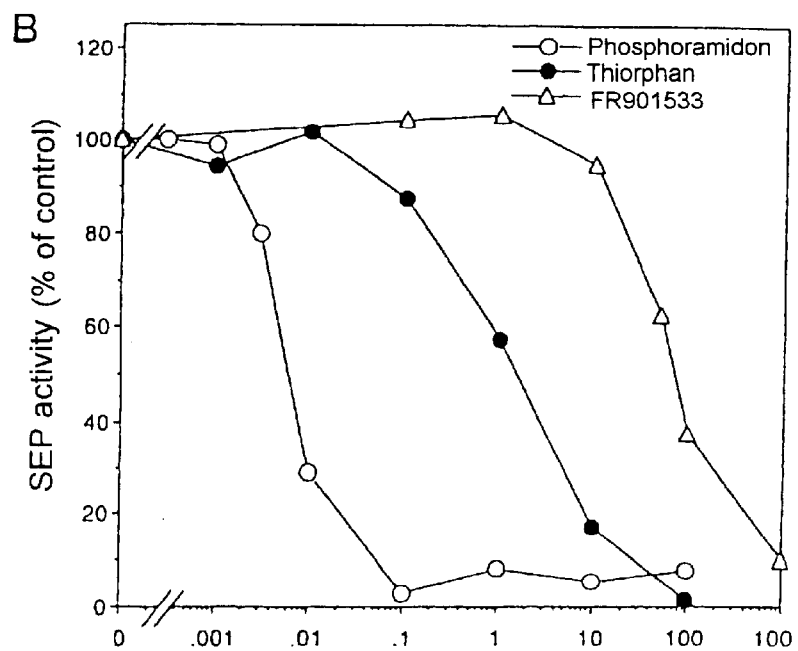
FIG. 9 is a graph showing inhibition of the soluble form of SEP by phosphoramidon, thiorphan and FR901533.
Figure 10:
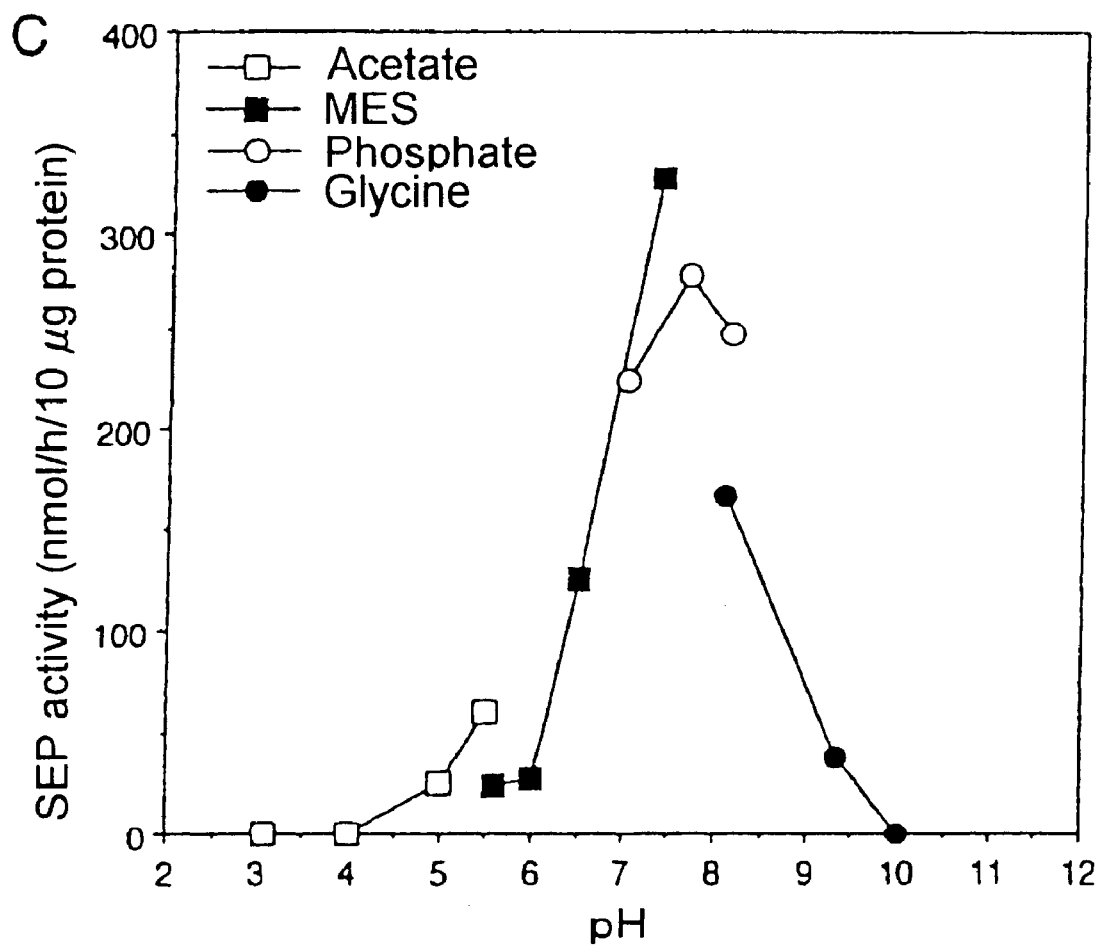
FIG. 10 is a graph showing the pH profile of the activity of the soluble from of SEP partially purified from the supernatant of CHO/SEP cells.

Both phosphoramidon and thiorphan inhibited SEP activity in a dose-dependent manner, with apparent $IC_{50}$ values of about 6 nM and 2 $\mu$M, respectively (FIG. 8). The enzyme was partially inhibited by the ECE specific inhibitor FR901533 and was not inhibited by the angiotensin-converting enzyme inhibitor captopril. A pH profiling study revealed a neutral optimal pH at 7.4, with a relatively sharp pH dependence (FIG. 10). These observations indicate that soluble form of SEP represents a novel metalloprotease with a neutral pH optimum and that it has an inhibitor sensitivity profile similar to that of NEP. Hydrolysis of a Variety of Bioactive Peptides by Recombinant Soluble Form of SEP:

Finally, the present inventors examined the SEP-catalyzed hydrolysis of other bioactive peptides that have been characterized as substrates of ECE-1 and/or NEP. Hydrolysis of the substrates was monitored by HPLC, and the results are summarized in Table 2. Percentage of hydrolysis was determined by comparing substance peak areas of control with SEP-digested samples.

TABLE 2

SEP Hydrolysis of Biologically Active Peptides

| Peptides | Hydrolysis (%) |
|---|---|
| Angiotensin I | >95 |
| Atrial Natriuretic peptide | >95 |
| Bradykinin | >95 |
| Big endothelin-1 | 42 |
| Endothelin-1 | 92 |
| Substance P | >95 |

The present inventors found that angiotensin I, ANP, bradykinin, and substance P were all digested to completion or near completion by soluble SEP, whereas a parallel preparation of the protein from untransfected CHO cells exhibited no detectable activity. These observations suggest that SEP possesses a broad substrate specificity that is similar to that of NEP.

Discussion

The present inventors have described that cloning and characterization of SEP, a novel soluble secreted metalloprotease that can hydrolyze a variety of vasoactive peptides.

The initial goal of the present inventors was to isolate another endothelin-converting enzyme, and the present inventors have demonstrated that SEP can cleave big ET-1 to produce mature ET-1 in vivo as well as in transfected cells. However, the present inventors feel that SEP does not qualify as a physiological ECE because it appears to hydrolyze ET-1 more efficiently than it produces ET-1 from big ET-1. Instead, many factors point to SEP sharing higher structural and functional similarities with NEP than with ECEs or other members of this metalloprotease family. First, the sequence identity of SEP with respect to NEP is higher than those of the other members. In particular, SEP and NEP are 42.7% identical to each other in their N-terminal portions (agnino acids 1–510 of SEP), whereas they only slightly resemble ECE-1, ECE-2, and XCE in this region. Second, the two arginine residues known to constitute the substrate binding sites in NEP ($Arg^{102}$ and $Arg^{747}$ in human NEP) are conserved in SEP ($Arg^{121}$ and $Arg^{764}$ in mouse SEP) [Turner, A. J. et al., FASEB J., 11:355–364(1997)]. In contrast, only one of the two arginine residues is conserved in ECE-1 ($Arg^{129}$ in human ECE-1b) and ECE-2 ($Arg^{162}$ in bovine ECE-2), although this has been shown to play an insignificant role in the substrate binding of ECE-1. Third, the residue $Cys^{412}$ in rat ECE-1, known to be involved in forming the dimeric structure of ECE-1, is not conserved in either SEP or NEP. Fourth, both SEP and NEP rapidly degrade big ET-1 and ET-1 at multiple internal cleavage sites, whereas ECE-1 cleaves specifically at the $Trp^{21}$-$Val^{22}$ bond of big ET-1 without cleaving other parts of big ET-1 or ET-1 [Xu, D. et al., Cell, 78:473–485(1994)]. Fifth, the activity of SEP is efficiently inhibited by the specific NEP inhibitor thiorphan but is not completely inhibitor FR901533. Finally, both SEP and NEP cleave many small peptides in a highly promiscuous manner. These finding suggest that SEP is not a physiologically relevant endothelin-converting enzyme and that SEP and NEP may constitute a subfamily within this group of metalloproteases.

Although SEP shares several important features with other known members of this metalloprotease family, it still exhibits striking differences from them. Transfection of an expression construct of SEP results in the release of a functional soluble form of the enzyme into the culture medium. This suggests that the soluble form of SEP may act as a circulating endopeptidase in vivo. These observations are in sharp contrast to the fact that both NEP and ECE act as membrane-bound enzymes, and neither releases a soluble form [Turner, A. J. et al., FASEB J., 11:355–364(1997)]. In fact, the present inventors are unaware of any member of this metalloprotease family that releases a functional soluble form of the enzyme. The endogenous proteolytic release of an integral membrane-bound ectoenzyme is well documented for angiotensin-converting enzyme (ACE), a member of another metalloprotease family, which plays a critical role in the maintenance of blood pressure in mammals. Although ACE exists primarily as a membrane-bound enzyme, a soluble form is present under normal conditions in many body fluids, including blood plasma. In mammals, ACE exists as two distinct isoenzymes, namely somatic and testicular ACE. They are derived from a single gene by alternative splicing. Transfection of the full-length cDNA of either the somatic or testicular isoenzyme results not only in the expression of the membrane-bound form of ACE on the cell surface but also in a secreted form as a result of proteolysis by some enzyme(s). However, SEP exhibits the following differences from ACE: (i) only one spliceoform of SEP expresses a soluble form of the enzyme, whereas both spliceoforms of ACE produce soluble forms of the enzyme; and (ii) membrane-bound ACE is expressed on the cell surface as an ectoenzyme, whereas membrane-bound SEP appears to be expressed in the early secretory pathway, including endoplasmic reticulum and a portion of the Golgi apparatus. Thus, although other metalloproteases are known to produce both forms, SEP is clearly a novel molecule.

What is claimed is:

1. A protein comprising the amino acid sequence set forth under SEQ ID NO:1 in the Sequence Listing, or a salt thereof.

2. A protein comprising the amino acid sequence set forth under SEQ ID NO:2 in the sequence Listing, or a salt thereof.

3. A DNA comprising a sequence encoding the protein of claim 1.

4. A DNA comprising a sequence encoding the protein of claim 2.

5. A DNA comprising the coding region nucleotide sequence of SEQ ID NO:3 or NO:4 in the Sequence Listing.

6. A DNA comprising a nucleotide sequence with one or more nucleotides substituted relative to the coding region nucleotide sequence of SEQ ID NO:3 or NO:4 in the Sequence Listing and encoding the protein encoded by the nucleotide sequence set forth under SEQ ID NO:3 or NO:4.

7. An expression vector in which the DNA of claim 5 is incorporated.

8. A transformant cell which carries an expression vector in which the DNA of claim 5 is incorporated.

9. A method for producing a protein which comprises introducing into a host cell an expression vector in which the DNA of claim 3 is incorporated to form a transformant, culturing the transformant to produce a protein encoded by the DNA, and collecting the protein.

* * * * *

UNITED STATES PATENT AND TRADEMARK OFFICE
CERTIFICATE OF CORRECTION

PATENT NO.    : 6,548,284 B1                                          Page 1 of 1
DATED         : April 15, 2003
INVENTOR(S)   : M. Matsuo et al.

It is certified that error appears in the above-identified patent and that said Letters Patent is hereby corrected as shown below:

Column 35,
Line 51, "sequence" should be -- Sequence --.
Lines 53 and 55, before "sequence" insert -- nucleotide --.
Line 60, "nucletide" should be -- nucleotide --.

Signed and Sealed this

Thirtieth Day of December, 2003

JAMES E. ROGAN
*Director of the United States Patent and Trademark Office*